(12) United States Patent
Wasik et al.

(10) Patent No.: US 9,486,469 B2
(45) Date of Patent: Nov. 8, 2016

(54) STAT5A AND ITS FUNCTIONAL TUMOR SUPPRESSOR ANALOGS FOR TREATMENT OF MALIGNANCIES EXPRESSING NPM/ALK AND OTHER ONCOGENIC KINASES

(75) Inventors: Mariusz A. Wasik, Ardmore, PA (US); Qian Zhang, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 412 days.

(21) Appl. No.: 12/681,327

(22) PCT Filed: Sep. 29, 2008

(86) PCT No.: PCT/US2008/078163
§ 371 (c)(1),
(2), (4) Date: Dec. 16, 2010

(87) PCT Pub. No.: WO2009/045965
PCT Pub. Date: Apr. 9, 2009

(65) Prior Publication Data
US 2011/0086043 A1 Apr. 14, 2011

Related U.S. Application Data

(60) Provisional application No. 60/960,471, filed on Oct. 1, 2007.

(51) Int. Cl.

| | |
|---|---|
| *A61K 31/7068* | (2006.01) |
| *A61K 31/7105* | (2006.01) |
| *A61K 31/713* | (2006.01) |
| *A61K 31/706* | (2006.01) |
| *A61K 31/5355* | (2006.01) |
| *A61K 38/17* | (2006.01) |
| *C12N 15/113* | (2010.01) |
| *C12Q 1/48* | (2006.01) |
| *G01N 33/574* | (2006.01) |

(52) U.S. Cl.
CPC ......... *A61K 31/706* (2013.01); *A61K 31/5355* (2013.01); *A61K 38/1709* (2013.01); *C12N 15/1135* (2013.01); *C12Q 1/485* (2013.01); *G01N 33/57484* (2013.01); *C12N 2310/11* (2013.01); *C12N 2310/14* (2013.01); *G01N 2333/91011* (2013.01); *G01N 2800/52* (2013.01)

(58) Field of Classification Search
CPC ........... A61K 31/5355; A61K 31/706; A61K 38/1709; C12N 15/1135; C12N 2310/11; C12N 2310/14; C12Q 1/485; G01N 2333/91011; G01N 2800/52; G01N 33/57484
USPC ................... 424/172.1, 93.7; 435/6.11, 6.14; 514/1.1, 44 A, 44 R, 49
See application file for complete search history.

(56) References Cited

U.S. PATENT DOCUMENTS

| | | |
|---|---|---|
| 5,770,421 A | 6/1998 | Morris et al. |
| 7,176,303 B2 | 2/2007 | Freier et al. |
| 2004/0234965 A1 | 11/2004 | Burgess |

OTHER PUBLICATIONS

Chiarle et al (Nature Medicine 11(6): 623-629, 2005).*
Chiarle et al (Nature Medicine 11(6): 623-629, 2005, Supplemental Fig. 6).*
Lin et al (Clin Cancer Res 2001;7:2880-2886).*
Yan et al (Cancer Biol Ther. 2(5): 552-556, 2003).*
Zhang et al (Proc. Nat. Acad. Sci. USA 102(19): 6948-6953, 2005).*
Nagasawa et al (Leukemia Research 30 (2006) 303-312).*
Santos et al (Endocrinology 149(1):329-338, 2008).*
Ziemecki (The EMBO Journal vol. 9 No. 1 pp. 1 91-1 96, 1990).*

* cited by examiner

*Primary Examiner* — Janet Epps-Smith
(74) *Attorney, Agent, or Firm* — Mark S. Cohen; Pearl Cohen Zedek Latzer Baratz LLP

(57) ABSTRACT

The invention provides methods of inhibiting epigenetic gene silencing in a cell expressing NPM/ALK or decreasing NPM/ALK content in a cell, by contacting a cell with an agent capable of increasing the concentration of Stat5a protein or its functional analog. Further, the invention provides a method of treating malignancies expressing oncogenic kinase by administering to a patient affected with a malignancy an agent capable of increasing the concentration of Stat5a protein or its epigenetically silenced functional tumor suppressor analog in a malignant cell. Finally, it provides a method to diagnose malignancy and monitor patient's response to therapy by analysis of the degree of DNA methylation of the gene encoding for Stat5a or its analog, their mRNA, or protein.

11 Claims, 6 Drawing Sheets

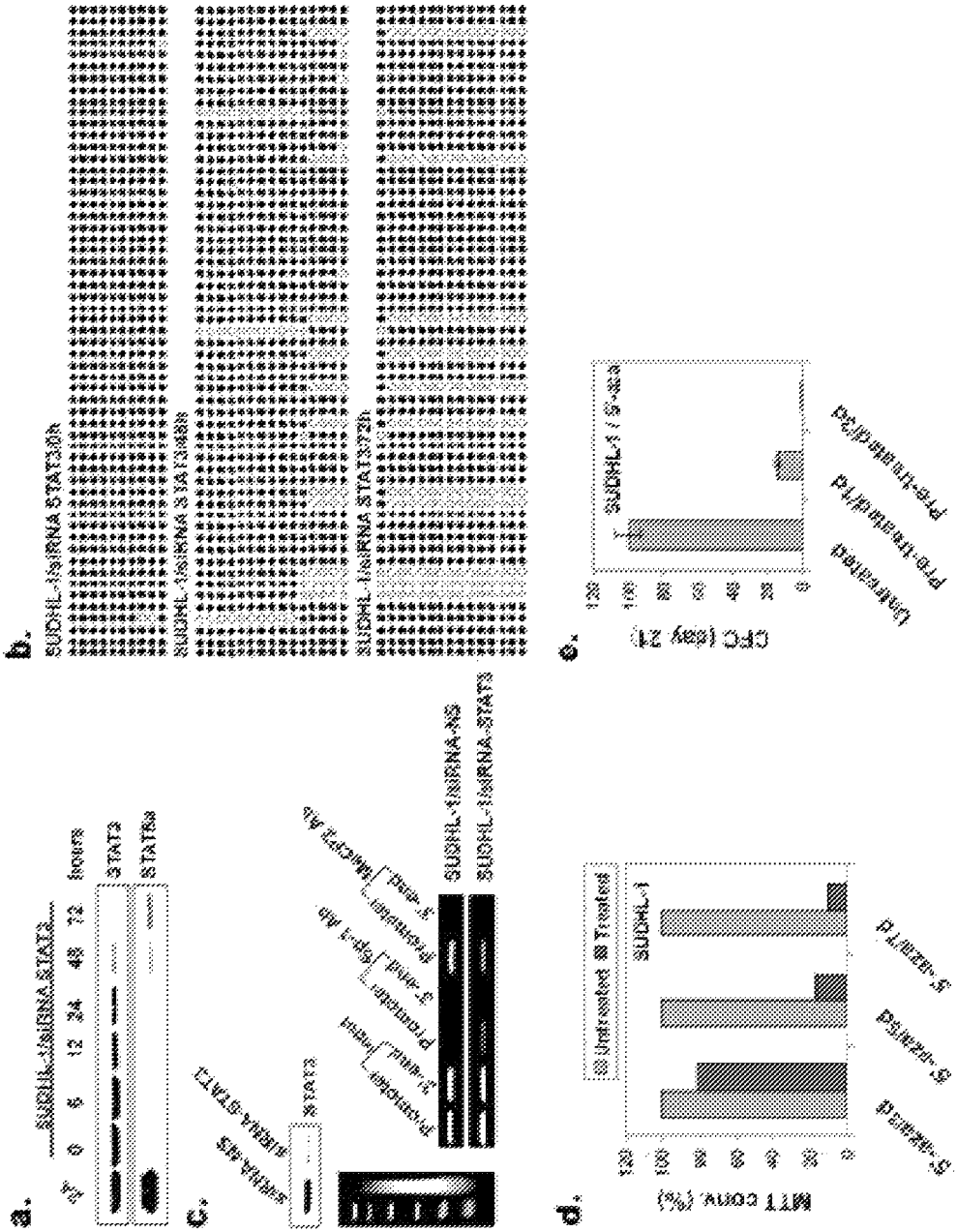

SEQUENCE LISTING

```
<160> NUMBER OF SEQ ID NOS: 23

<210> SEQ ID NO 1
<211> LENGTH: 4298
<212> TYPE: DNA
<213> ORGANISM: Homo sapiens

<400> SEQUENCE: 1
cagacaggat attcactgct gtggcaaggc ctgtagagag tttcgaagtt aggaggactc    60
aagacggtcc ctccctggac ttttctgaag gggctcaaaa gatgacacgc gccagagctg   120
gaaggcgtcg ccaattggtc caactttcc ctcctccctt tttgcggatg agaaaaactg    180
aggcccaggt ttgggatttc cagagcccgg gatttcccgg caacgccgac aaccacattc    240
ccccggctat tctgacccgc cccggttccg ggacgctccc tgggagccgc cgccgagggc    300
ctgctgggac tcccggggac cccgccgtcg gggcagcccc cacgcccggc gccgcccgcc    360
ggaacggcgc cgctgttgcg cacttgcagg ggagccggcg actgagggcg aggcagggag    420
ggagcaagcg gggctgggag ggctgctggc gcgggctcgc cggctgtgta tggtctatcg    480
```

```
caggcagctg acctttgagg aggaaatcgc tgctctccgc tccttcctgt agtaacagcc    540
gccgctgccg ccgccgccag gaaccccggc cgggagcgag agccgcgggg cgcagagccg    600
gcccggctgc cggacggtgc ggccccacca ggtgaacggc catggcgggc tggatccagg    660
cccagcagct gcagggagac gcgctgcgcc agatgcaggt gctgtacggc cagcacttcc    720
ccatcgaggt ccggcactac ttggcccagt ggattgagag ccagccatgg gatgccattg    780
acttggacaa tccccaggac agagcccaag ccacccagct cctggagggc ctggtgcagg    840
agctgcagaa gaaggcggag caccaggtgg gggaagatgg gtttttactg aagatcaagc    900
tggggcacta cgccacgcag ctccagaaaa catatgaccg ctgcccctg gagctggtcc    960 gctgcatccg gcacattctg tacaatgaac agaggctggt ccgagaagcc aacaattgca   1020
gctctccggc tgggatcctg gttgacgcca tgtcccagaa gcaccttcag atcaaccaga   1080
catttgagga gctgcgactg gtcacgcagg acacagaga tgagctgaag aaactgcagc   1140
agactcagga gtacttcatc atccagtacc aggagagcct gaggatccaa gctcagtttg   1200
cccagctggc ccagctgagc ccccaggagc gtctgagccg ggacggcc ctccagcaga   1260 agcaggtgtc tctggaggcc tggttgcagc gtgaggcaca gacactgcag cagtaccgcg   1320
tggagctggc cgagaagcac cagaagaccc tgcagctgct gcggaagcag cagaccatca   1380
tcctggatga cgagctgatc cagtggaagc ggcggcagca gctggccggg aacggcgggc   1440
cccccgaggg cagcctggac gtgctacagt cctggtgtga agttggcc gagatcatct   1500 ggcagaaccg gcagcagatc cgcagggctg agcacctctg ccagcagctg cccatccccg   1560
gcccagtgga ggagatgctg gccgaggtca acgccaccat cacggacatt atctcagccc   1620
tggtgaccag cacattcatc attgagaagc agcctcctca ggtcctgaag cccagacca   1680 agtttgcagc caccgtacgc ctgctggtgg gcgggaagct gaacgtgcac atgaatcccc   1740
cccaggtgaa ggccaccatc atcagtgagc agcaggccaa gtctctgctt aaaaatgaga   1800
acacccgcaa cgagtgcagt ggtgagatcc tgaacaactg ctgcgtgatg gagtaccacc   1860
aagccacggg cacccctcagt gcccacttca ggaacatgtc actgaagagg atcaagcgtg   1920
ctgaccggcg gggtgcagag tccgtgacag aggagaagtt cacagtcctg tttgagtctc   1980
agttcagtgt tggcagcaat gagcttgtgt tccaggtgaa gactctgtcc ctacctgtgg   2040
ttgtcatcgt ccacggcagc caggaccaca atgccacggc tactgtgctg tgggacaatg   2100
cctttgctga gccgggcagg gtgccatttg ccgtgcctga caaagtgctg tggccgcagc   2160
tgtgtgaggc gctcaacatg aaattcaagg ccgaagtgca gagcaaccgg ggcctgacca   2220
aggagaacct cgtgttcctg gcgcagaaac tgttcaacaa cagcagcagc cacctggagg   2280
actacagtgg cctgtccgtg tcctggtccc agttcaacag ggagaacttg ccgggctgga   2340
actacacctt ctggcagtgg tttgacgggg tgatggaggt gttgaagaag caccacaagc   2400
cccactggaa tgatgggggcc atcctaggtt ttgtgaataa gcaacaggcc cacgacctgc   2460
tcatcaacaa gcccgacggg accttcttgt tgcgctttag tgactcagaa atcgggggca   2520
tcaccatcgc ctggaagttt gactccccgg aacgcaacct gtggaacctg aaaccattca   2580
ccacgcggga tttctccatc aggtccctgg ctgaccggct ggggacctg agctatctca   2640 tctatgtgtt tcctgaccgc cccaaggatg aggtcttctc caagtactac actcctgtgc   2700
tggctaaagc tgttgatgga tatgtgaaac cacagatcaa gcaagtggtc cctgagtttg   2760
tgaatgcatc tgcagatgct gggggcagca gcgccacgta catggaccag gccccctccc   2820
cagctgtgtg ccccccaggct ccctataaca tgtacccaca gaaccctgac catgtactcg   2880
```

-continued

```
atcaggatgg agaattcgac ctggatgaga ccatggatgt ggccaggcac gtggaggaac    2940
tcttacgccg accaatggac agtcttgact cccgcctctc gcccctgcc ggtcttttca     3000 cctctgccag aggctccctc tcatgaatgt ttgaatccca cgcttctctt tggaaacaat    3060
atgcaatgtg aagcggtcgt gttgtgagtt tagtaaggtt gtgtacactg acacctttgc   3120
aggcatgcat gtgcttgtgt gtgtgtgtgt gtgtgtgtcc ttgtgcatga gctacgcctg    3180
cctcccctgt gcagtcctgg gatgtggctg cagcagcggt ggcctctttt cagatcatgg    3240
catccaagag tgcgccgagt ctgtctctgt catggtagag accgagcctc tgtcactgca    3300
ggcactcaat gcagccagac ctattcctcc tgggcccctc atctgctcag cagctatttg    3360
aatgagatga ttcagaaggg gaggggagac aggtaacgtc tgtaagctga gtttcactc    3420 cggagtgaga agctttgccc tcctaagaga gagagacaga gagacagaga gagagaaaga    3480
gagagtgtgt gggtctatgt aaatgcatct gtcctcatgt gttgatgtaa ccgattcatc    3540
tctcagaagg gaggctgggg gttcattttc gagtagtatt ttatacttta gtgaacgtgg    3600
actccagact ctctgtgaac cctatgagag cgcgtctggg cccggccatg tccttagcac    3660
aggggggccg ccggtttgag tgagggtttc tgagctgctc tgaattagtc cttgcttggc    3720
tgcttggcct tgggcttcat tcaagtctat gatgctgttg cccacgtttc ccgggatata    3780
tattctctcc cctccgttgg gccccagcct tctttgcttg cctctctgtt tgtaaccttg    3840
tcgacaaaga ggtagaaaag attgggtcta ggatatggtg ggtggacagg ggccccggga   3900
cttggagggt tggtcctctt gcctcctgga aaaacaaaa acaaaaaact gcagtgaaag     3960
acaagctgca aatcagccat gtgctgcgtg cctgtggaat ctggagtgag gggtaaaagc    4020
tgatctggtt tgactccgct ggaggtgggg cctggagcag gccttgcgct gttgcgtaac    4080
tggctgtgtt ctggtgaggc cttgctccca accccacacg ctcctccctc tgaggctgta    4140
ggactcgcag tcaggggcag ctgaccatgg aagattgaga gcccaaggtt taaacttctc    4200
tgaagggagg tggggatgag aagagggggtt tttttgtact ttgtacaaag accacacatt   4260
tgtgtaaaca gtgttttgga ataaaatatt tttttcat                           4298
```

<210> SEQ ID NO 2
<211> LENGTH: 21
<212> TYPE: DNA
<213> ORGANISM: Homo sapiens

<400> SEQUENCE: 2
aaatggcggg ctggatccag g         21

<210> SEQ ID NO 3
<211> LENGTH: 20
<212> TYPE: DNA
<213> ORGANISM: Homo sapiens

<400> SEQUENCE: 3
agcgtgggat tcaaacattc           20

<210> SEQ ID NO 4
<211> LENGTH: 21
<212> TYPE: DNA
<213> ORGANISM: Homo sapiens

<400> SEQUENCE: 4
ccactgctta ctggcttatc g         21

```
<210> SEQ ID NO 5
<211> LENGTH: 18
<212> TYPE: DNA
<213> ORGANISM: Homo sapiens

<400> SEQUENCE: 5
ccgccagtgt gatggata                                                 18

<210> SEQ ID NO 6
<211> LENGTH: 19
<212> TYPE: DNA
<213> ORGANISM: Homo sapiens

<400> SEQUENCE: 6
gtacagcacc tgcatctgg                                                19

<210> SEQ ID NO 7
<211> LENGTH: 25
<212> TYPE: DNA
<213> ORGANISM: Homo sapiens

<400> SEQUENCE: 7
taatttaggg gtttaaaaga tgata                                         25

<210> SEQ ID NO 8
<211> LENGTH: 20
<212> TYPE: DNA
<213> ORGANISM: Homo sapiens

<400> SEQUENCE: 8
acctaataaa accgcaccgt                                               20

<210> SEQ ID NO 9
<211> LENGTH: 20
<212> TYPE: DNA
<213> ORGANISM: Homo sapiens

<400> SEQUENCE: 9
acctaataaa acctcaccTT                                               20

<210> SEQ ID NO 10
<211> LENGTH: 25
<212> TYPE: DNA
<213> ORGANISM: Homo sapiens

<400> SEQUENCE: 10
gagtattcta agaaatggat ttgca                                         25

<210> SEQ ID NO 11
<211> LENGTH: 18
<212> TYPE: DNA
<213> ORGANISM: Homo sapiens

<400> SEQUENCE: 11
cacattcccc cggctatt                                                 18

<210> SEQ ID NO 12
<211> LENGTH: 23
<212> TYPE: DNA
<213> ORGANISM: Homo sapiens

<400> SEQUENCE: 12
aaaagagtcc ttcctgtctc gac                                           23
```

<210> SEQ ID NO 13
<211> LENGTH: 40
<212> TYPE: DNA
<213> ORGANISM: Homo sapiens

<400> SEQUENCE: 13
ctggctcctt acccttctga ctggctcctt acccttctga                              40

<210> SEQ ID NO 14
<211> LENGTH: 20
<212> TYPE: DNA
<213> ORGANISM: Homo sapiens

<400> SEQUENCE: 14
gcctcagctt tccaagtagc                                                    20

<210> SEQ ID NO 15
<211> LENGTH: 19
<212> TYPE: DNA
<213> ORGANISM: Homo sapiens

<400> SEQUENCE: 15
tgcctgctac ttactgtgc                                                     19

<210> SEQ ID NO 16
<211> LENGTH: 20
<212> TYPE: DNA
<213> ORGANISM: Homo sapiens

<400> SEQUENCE: 16
ggctccttca caaaccagag                                                    20

<210> SEQ ID NO 17
<211> LENGTH: 20
<212> TYPE: DNA
<213> ORGANISM: Homo sapiens

<400> SEQUENCE: 17
atgaacccat gctcaaaacc                                                    20

<210> SEQ ID NO 18
<211> LENGTH: 29
<212> TYPE: DNA
<213> ORGANISM: Homo sapiens

<400> SEQUENCE: 18
aaggtaccaa atggcgggct ggatccagg                                          29

<210> SEQ ID NO 19
<211> LENGTH: 29
<212> TYPE: DNA
<213> ORGANISM: Homo sapiens

<400> SEQUENCE: 19
ttaagcttcg atggaagatt cgatggaca                                          29

<210> SEQ ID NO 20
<211> LENGTH: 32
<212> TYPE: DNA
<213> ORGANISM: Homo sapiens

<400> SEQUENCE: 20

-continued

```
aagcggccgc gctcagggcc caggctggtt ca                              32

<210> SEQ ID NO 21
<211> LENGTH: 19
<212> TYPE: DNA
<213> ORGANISM: Homo sapiens

<400> SEQUENCE: 21
acattccccc ggctattct                                             19

<210> SEQ ID NO 22
<211> LENGTH: 28
<212> TYPE: DNA
<213> ORGANISM: Homo sapiens

<400> SEQUENCE: 22
actctagaag cgtgggattc aaacattc                                   28

<210> SEQ ID NO 23
<211> LENGTH: 9
<212> TYPE: DNA
<213> ORGANISM: Homo sapiens

<400> SEQUENCE: 23 ttctaagaa                                                         9
```

STAT5A AND ITS FUNCTIONAL TUMOR SUPPRESSOR ANALOGS FOR TREATMENT OF MALIGNANCIES EXPRESSING NPM/ALK AND OTHER ONCOGENIC KINASES

CROSS-REFERENCE TO RELATED APPLICATIONS

This is a national phase application of PTC international application PTC/US08/78163, filed Sep. 29, 2008, that claims priority to U.S. provisional patent application 60/960,471, filed 01 Oct. 2007, which is incorporated by reference herein in its entirety.

FIELD OF THE INVENTION

The present invention provides methods and compositions for treating malignancies associated with the expression of oncogenic tyrosine kinase. Specifically, the invention provides methods and compositions for the treatment of malignancies associated with oncogenic kinase using Stat5a and its functional analog.

BACKGROUND OF THE INVENTION

The STAT5 proteins are involved in key cell functions including proliferation, differentiation and survival. Persistent STAT5 activation occurs in malignant cells of both hematopoietic and nonhematopoietic origin. There are two separate STAT5 proteins, STAT5a and STAT5b that are encoded by two closely related genes. Although the proteins have 94% sequence identity, gene knockout mouse models showed that STAT5a and STAT5b have certain distinct, non-overlapping functions. The exact role of STAT5a as opposed to STAT5b in malignant cell transformation is much less well understood.

Epigenetic gene silencing performs an important function in carcinogenesis by inhibiting expression of many tumor-suppressor genes. Methylation of the CpG islands in the gene promoter region is the key component of the process. CpG methylation is mediated by members of the DNA methyltransferase (DNMT) family that can be inactivated by small-molecule inhibitors such as 5'-aza-2'-deoxy-cytidine (5'-aza). Another class of proteins, designated MBD, also plays a key part in epigenetic gene silencing by binding to the methylated CpG sites and interfering with binding of transcription activators. One member of this group, MeCP2, is capable of binding to single CpG sites.

Normally, ALK tyrosine kinase expression seems confined to neural cells. Its ectopic expression in a subset of T-cell lymphomas (ALK$^+$ TCL) and other malignancies typically results from chromosomal translocations involving the ALK gene and various partners, for example the nucleophosmin (NPM1) or echinoderm microtubule-associated protein-like 4 (EML4) gene. The NPM-ALK protein contains the NPM oligomerization motif and the ALK catalytic domain, is constitutively activated through autophosphorylation, and mediates malignant cell transformation in vitro and in vivo by activating downstream effectors including STAT3.

SUMMARY OF THE INVENTION

In one embodiment, the present invention provides a method of inhibiting epigenetic gene silencing in a cell expressing NPM/ALK, another form of ALK, or another chimeric tyrosine kinase, comprising the step of contacting the cell or subject with an effective amount of an agent capable of increasing the amount of Stat5a protein or its functional tumor suppressor analog in the cell.

In another embodiment, the invention provides a method of decreasing NPM/ALK, or another oncogenic-kinase content in a cell, comprising the step of contacting a cell expressing NPM/ALK or another oncogenic-kinase, with an effective amount of an agent capable of increasing the amount of Stat5a or its functional analog, thereby down-regulating the kinase gene expression in the cell.

In another embodiment, the present invention provides a method of treating malignancies expressing oncogenic kinase in a cell or subject, comprising the step of administering to the subject a composition comprising an agent capable of increasing the amount of Stat5a protein or its analog in the cell.

In one embodiment, the invention provides a method of treating malignancies in a subject comprising the step of contacting the subject with a therapeutically effective amount of a composition comprising Stat5a DNA, mRNA, or protein, thereby suppressing tumor growth.

In another embodiment, the present invention provides a method of preventing, inhibiting or suppressing epigenetic silencing of transcriptional expression of a tumor suppressor in a subject, comprising the step of contacting the subject with a therapeutically effective amount of a agent capable of increasing the amount of STAT5a tumor suppressor functional analog which inhibits expression or function of an oncogenic kinase.

In one embodiment, the present invention provides a method of treating, inhibiting or suppressing, or ameliorating symptoms associated with a T-cell lymphoma in a subject, comprising the step of administering to the subject a therapeutically effective amount of a composition comprising an agent capable of increasing the expression or function of Stat5a protein or its analog thereby treating, inhibiting or suppressing, or ameliorating symptoms associated with T-cell lymphoma in the subject.

In another embodiment, the invention provides a method of providing a diagnosis for the presence of a malignancy associated with expression of chimeric tyrosine kinase in a subject, comprising the step of: obtaining a biological sample from the subject, analyzing the expression level of: Stat5a, Stat3, NPM/ALK or their combination; and comparing the expression level with a standard.

In one embodiment, the invention provides a method of providing a prognosis for the severity of a malignancy associated with expression of chimeric tyrosine kinase in a subject, comprising the step of: obtaining a biological sample from the subject, analyzing the expression level of: Stat5a, Stat3, NPM/ALK or their combination; and comparing the expression level with a standard.

In another embodiment, the invention provides a method of evaluating the effectiveness of a treatment regimen for a malignancy associated with expression of chimeric tyrosine kinase, comprising the step of: obtaining a biological sample from the subject; analyzing the expression level of: Stat5a, Stat3, NPM/ALK or their combination; and comparing the expression level with a standard.

In one embodiment, the invention provides a method of providing a diagnosis for the presence of a malignancy associated with expression of chimeric tyrosine kinase, or evaluating a treatment effectiveness in a subject, comprising the step of: obtaining a biological sample from the subject, analyzing the degree of methylation in the CpG island within the Stat5a gene promoter region; and comparing the degree of methylation with a standard taken from the same biological sample of a healthy subject or pool of subjects.

BRIEF DESCRIPTION OF THE DRAWINGS

The invention will be better understood from a reading of the following detailed description taken in conjunction with the drawings in which like reference designators are used to designate like elements, and in which:

FIG. 1a: depicts a gel showing that the T-cell population examined were normal, T-cell rich peripheral blood mononuclear cells (PBMC), mitogen (PHA)-activated PBMC (PBMC/PHA-blasts), and PHA- and IL-2-activated PBMC (PBMC/PHA-blasts/IL-2), and malignant T-cell lymphoma cell lines from NPM/ALK-cutaneous T-cell lymphoma (CTCL; 2A cell line) and NPM/ALK$^+$ T-cell lymphoma (ALK+TCL; JB6, SUHDL-1, and SUP-M2). Expression of Stat5a, NPM/ALK, Stat5b, and actin was determined by Western blotting. FIG. 1b: depicts a gel showing a Western blot-detected expression of Stat5a protein in the depicted malignant T-cell lymphoma cell lines (upper panel) representing CTCL, adult-type T-cell lymphoma/leukemia (ATLL), and acute T-cell leukemia/lymphoblastic lymphoma (ATCL). Lower panel: B-cell lines derived from Epstein-Barr virus transformed PBMC (EBV+LCL), mantle cell lymphoma (MCL), diffuse large B-cell lymphoma (DLBCL), and Burkitt lymphoma (BL). Normal PBMC served as a control. FIG. 1c: depicts a gel showing the analysis of Stat5a protein expression in primary lymphoma cells from patients (pt) with ALK+TCL (left panel) and advanced CTCL (right panel). CTCL-derived 2A and ALK+TCL-derived JB6 and SUDHL-1 cell lines served as controls. Examination of expression of Stat5b, NPM/ALK, Stat3, and actin was used as additional control. FIG. 1d: depicts a gel showing the stimulation of the NPM/ALK$^+$ T cell line, SUDHL-1 with PHA and PHA/IL-2 to induce expression of Stat5a protein. PBMC and PBMC/PHA-blasts served as positive controls of Stat5a protein expression, actin served as control of protein concentration. FIG. 1e: depicts a gel showing the Lack of Stat5a mRNA expression in NPM/ALK$^+$ T cells. Left panel: normal PBMC and NPM/ALK$^-$ (2A) and NPM/ALK$^+$ (SUDHL-1, SUP-M2, and JB6) malignant T cells were evaluated by RT-PCR for expression of Stat5a mRNA. RT-PCR with primers specific for actin served as positive control. Right panel: stimulation of the SUDHL-1 cell line with PHA and PHA/IL-2 to induce Stat5a mRNA expression. 2A cell line served as positive control of Stat5a mRNA expression, actin as positive control of mRNA quality.

FIG. 2a: is a scheme showing the structure of the human Stat5a gene. The diagram depicts the exon-intron boundaries and the CpG island. The part of the CpG island examined by bisulfate-aided DNA sequence analysis contains 57 CpG sites (open-circle lollipops). The arrows indicate attachment sites of the PCR primers used for the DNA sequence analysis. FIG. 2b: shows the DNA sequence analysis of the Stat5a gene CpG island. The analysis was performed in PBMC from a healthy donor (H. D. #1; similar results were obtained from three other healthy donors and an NPM/ALK$^-$ CTCL cell line 2A), NPM/ALK$^+$ T-cell lines SUDHL-1 (JB6, and SUP-M2) and tissue samples from four patients with ALK$_+$ T cell lymphoma (pt #1-4). The open-circle lollipops depict unmethylated cytosines and the solid-dot lollipops depict methylcytosines within the CpG sites. Four to 6 separate cloned DNA fragments were analyzed per population studied including 6 clones per each patient sample; the representative results are presented. FIG. 2c: depicts a gel showing the lack of binding of Sp-1 transcription activator to the Stat5a gene promoter in NPM/ALK$^+$ T cells. Cell lysates from NPM/ALK$^+$ T cells (SUDHL-1; right panel) and control, normal PBMC/PHA-blasts (left panel) were examined by ChIP assay using antibodies reactive with Sp-1 and PCR primer pairs corresponding to promoter and 3'-end of the Stat5a gene. The whole, non-immunoprecipitated cell lysate (input) served as positive control. FIG. 2d: depicts a gel showing the binding of MeCP2 CpG-binding protein to the Stat5a gene promoter in NPM/ALK$^+$ T cells. Cell lysates from SUDHL-1 (right panel) and PBMC/PHA-blasts (left panel) were examined by ChIP assay using MeCP2-reactive antibody and the Stat5a gene promoter and 3'-end primers.

FIG. 3a: depicts a gel showing the kinetics of RT-PCR-detected expression of Stat5a mRNA at the depicted time points. PBMC/PHA-blasts and actin served as positive controls of quality of Stat5a primers and mRNA, respectively. FIG. 3b: shows the sequence analysis of bisulfate-modified DNA from the CpG island of the Stat5a promoter region, before (upper panel) and after (lower panel) cell treatment with 5'-aza. The diagrams show the changes of methylation Status in 57 CpG sites in the six separate DNA clones per panel: solid dots depict methylcytosines and open circles unmethylated cytosines. The boxes highlight the CpG sites located within binding sites of the Sp-1 transcription activator. FIG. 3c: depicts a gel showing the binding of Sp-1 to Stat5a promoter. Lysates from SUDHL-1 cells, either untreated or treated with 5'-aza for 5 days, were examined in the ChIP assay using antibody reactive with Sp-1 and PCR primer pairs corresponding to Stat5a promoter and 3'-end of the Stat5a gene. FIG. 3d: depicts a gel showing the expression of Stat5a is associated with inhibition of NPM/ALK expression. SUDHL-1 cells treated with the DNMT inhibitor 5'-aza for up to 7 days were harvested at 1-day intervals and analyzed by Western blotting for expression of Stat5a, NPM/ALK, phospho(P)-Stat3, total STAT3, and actin. FIG. 3e: depicts a gel showing the inhibition of NPM/ALK expression is Sta5a dependent. A subset of the 5'-aza-treated SUDHL-1 cells was transfected with either Stat5a-specific or non-targeting siRNA on day 3 of the treatment and examined on days 4 and 5 for expression of Stat5a, NPM/ALK, and the other depicted proteins.

FIG. 4a: a schematic map of the NPM/ALK gene promoter and enhancer regions. FIG. 4b: depicts a gel showing the binding of Stat5a to enhancer region of the NPM/ALK gene. The nuclear protein extracts from SUDHL-1 cells either untreated or treated for 5 days with 5'-aza were incubated with biotin-labeled, 25-base oligonucleotide probe corresponding to the wildtype (WT) Stat5a-binding site (TTCTAAGAA) and analyzed in EMSA (upper left panel). As a specificity control, protein extract of the 5'-aza-treated cells was pre-incubated with 25-fold excess of the unlabeled (cold) probe (designated c. probe). The same SUDHL-1 extracts from 5'-aza-treated cells were also analyzed in EMSA using probes with STAT5a binding site mutants (M) with the depicted 3-base substitutions of either the TTC or the GAA backbone (upper right panel). Lower panel: SUDHL-1 cells, either untreated or treated for 5 days with 5'-aza, were analyzed in ChIP assay using anti-Stat5a antibody and two sets of primers specific for either NPM/ALK gene enhancer region or 3' end. FIG. 4c: depicts a gel showing the binding of transfected Stat5a to the NPM/ALK gene enhancer. SUDHL-1 cells were transiently transfected with pcDNA3-Stat5a or pcDNA3 vector alone. RT-PCR-examined expression of pcDNA3 (upper left panel) and Stat5a (lower left panel). Right panel: EMSA with biotin-labeled or unlabeled (c. probe) 25-mer oligonucleotide probes containing the NPM/ALK gene enhancer's Stat5a-binding site. Lower panel: ChIP assay using the anti-Stat5a antibody and primer sets specific for either the enhancer or 3' end of the gene. FIG. 4d: depicts a gel showing the inhibition of NPM/ALK expression by transfected Stat5a. SUDHL-1 cells transiently transfected with pcDNA3-hStat5a or empty pcDNA3 vector were analyzed by Western blotting for expression of Stat5a, NPM/ALK, phospho(P)-Stat3, total STAT3 and actin. PBMC/PHA-blasts stimulated with IL-2 served as a control. FIG. 4e: Selective inhibition of NPM/ALK expression by Stat5a. SUDHL-1 cells, untreated, treated for 5 days with 5'-aza, or transfected with pcDNA3-Stat5a, were analyzed by Western blotting using an antibody against the N-terminus of NPM that recognizes both native NPM and chimeric NPM/ALK. Detection of Stat5a protein expression served as a control. FIG. 4f: depicts a gel showing the binding of Stat5a to exon 14 of the NPM/ALK gene in vitro. EMSA of the protein extracts from SUDHL-1 cells either untreated or 5'-aza-treated were incubated with labeled oligonucleotide probe corresponding to the wild type (WT), Stat5a-binding site (TTCTGAGAA). Pre-incubation with the unlabeled (cold) probe (C. probe), probe with the site mutant (MT) with the substitution of the TTC with CCG, or Stat5a antibody (the super-shifted band is marked by an arrow), served as controls. FIG. 4g: depicts a gel showing the binding of Stat5a to exon 14 of the NPM/ALK gene in vivo. Stat5a binding to exon 14 region that contains the identified binding site candidate was examined by ChIP in 5'-aza-treated SUDHL-1 cells.

FIG. 5a: depicts a gel showing the effect of NPM/ALK depletion on expression of Stat5a. SUDHL-1 were treated with ALK siRNA- or control, non-targeting siRNA and analyzed at 48 hr for expression of NPM/ALK, Stat5a, and actin proteins (left panel) and in vivo binding of Sp-1 transcription factor to the Stat5a gene promoter (right panel). FIG. 5b: depicts a gel showing the inhibition of Stat5a expression in NPM/ALK-cells by transfected NPM/ALK. The B- and T-cell lines (BJAB and 2B and Jurkat, respectively) transfected with NPM/ALK-containing or empty pcDNA3 vector were analyzed after 72 hr for expression of NPM/ALK and Stat5a proteins with actin and native NPM serving as positive controls. FIG. 5c: depicts a gel showing the efficiency of cell transfection. Flow cytometry (left panel) and immunofluorescence microscopy (right panel) examination of Jurkat cells transfected with an empty or GFPcontaining vector (24 hr time point). FIG. 5d: depicts a gel showing the time course of Stat5a protein loss due to NPM/ALK expression. Expression of the listed proteins was analyzed at the depicted time points in NPM/ALK-transfected Jurkat cells. FIG. 5e: depicts a map showing the effect of NPM/ALK expression on methylation status of the Stat5a gene promoter. DNA from empty vector- or NPM/ALK-transfected Jurkat cells was collected at the indicated time points, cloned and sequence analyzed for CpG island methylation of the Stat5a gene promoter and, as controls, SHP-1 and APAF-1 gene promoters. The opencircle lollipops depict unmethylated cytosines and the solid-dot lollipops depict methylcytosines.

FIG. 6. shows that Stat3-mediated inhibition of Stat5a gene expression and effect of DNMT inhibition on growth of the NPM/ALK$^+$ T cells. SUDHL-1 cells were treated with Stat3 siRNA- or control, non-targeting (NS) siRNA and analyzed at 48 hr and the other depicted time points for expression of Stat3 and Stat5a proteins (the gel depicted in FIG. 6a), changes in methylation of the Stat5a gene promoter (the map depicted in FIG. 6b) and in vivo binding of Sp-1 transcription activator and MeCP2 capping protein to the Stat5a promoter (the gel depicted in FIG. 6c). FIG. 6d: depicts a bar graph showing a triplicate SUDHL-1 cell cultures that were treated with 5'-aza or medium alone for 3, 5, and 7 days with fresh medium added every two days. The cells were pulsed with the MTT substrate for the last 4 hr of the culture. FIG. 6e: depicts a bar graph showing that SUDHL-1 cells were either untreated or treated in triplicate cultures for 1 or 3 days with 5'-aza and analyzed in the colony formation assay on day 21. The results are depicted as percentage with reference to the number of colonies formed by the untreated cells.

DETAILED DESCRIPTION OF THE INVENTION

Figure 1:
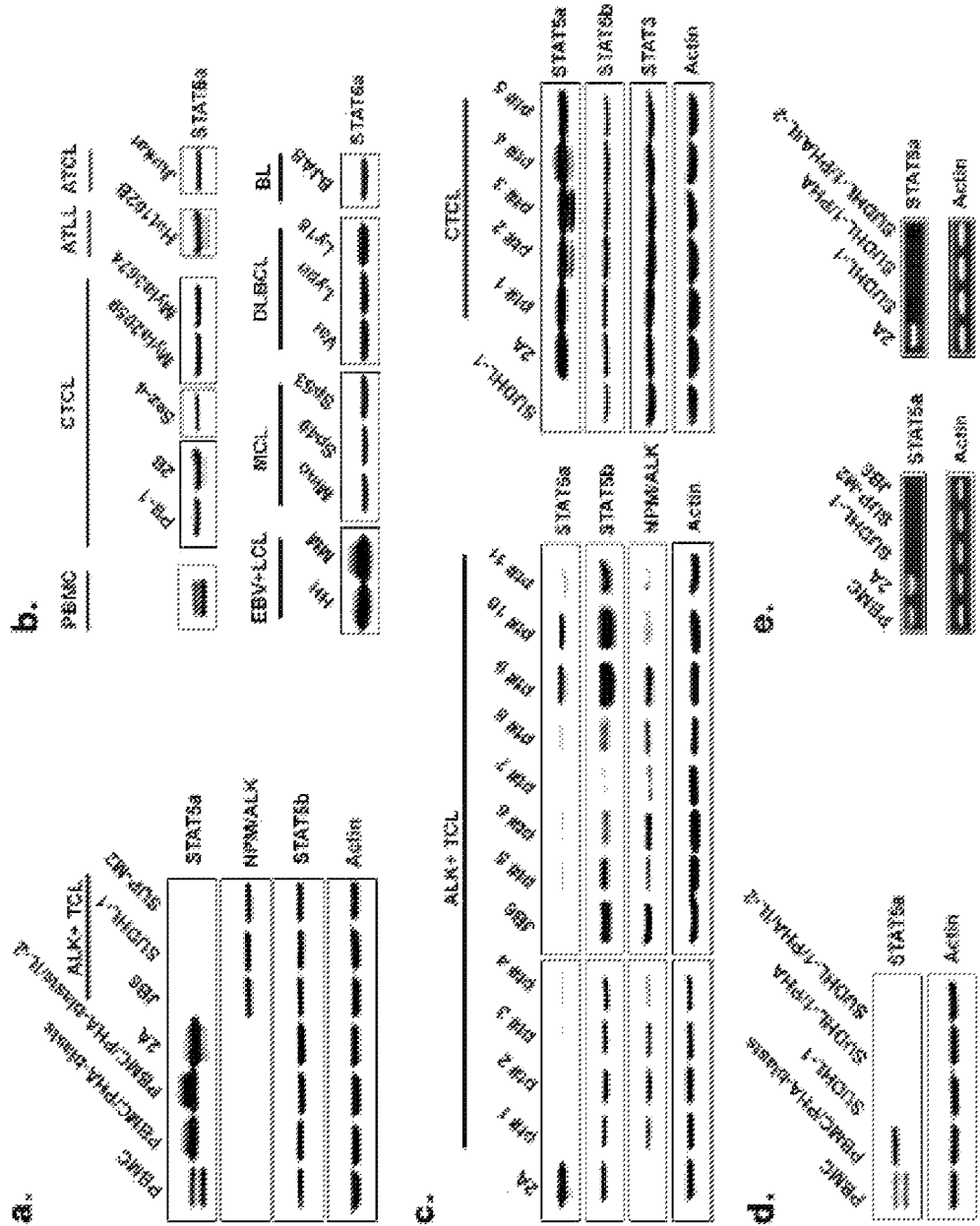
FIG. 1. shows the Lack of Stat5a expression in NPM/ALK$^+$ T cells.

In one embodiment, provided herein are methods and compositions for treating malignancies associated with the expression of oncogenic kinase. In another embodiment, described herein are methods and compositions for the treatment of malignancies associated with oncogenic kinase using Stat5a or its functional analog.

STAT3 and STAT5 are recognized in certain embodiments as oncoproteins, and their persistent activation is present in a large spectrum of lymphoid and nonlymphoid malignancies. In another embodiment, Stat3 and Stat5 promote oncogenesis by modulating several key functions of the malignant cells, such as survival, proliferation, migration, invasion, induction of angiogenesis, and evasion of the immune response. In breast carcinoma, STAT5 phosphorylation confers a good prognosis in one embodiment, resulting from inhibition of the metastatic capacity of the malignant cells, which STAT5 mediates in another embodiment by promoting expression of E-cadherin, indicating that STAT5 inhibits in certain embodiments, rather than promotes oncogenesis.

In another embodiment, STAT5a protein acts directly as a tumor suppressor by targeting expression of a key oncogene. In one embodiment, expression of STAT5a is lost in malignant cells, in this case in T lymphocytes transformed by NPM/ALK tyrosine kinase, and in another embodiment, that loss of STAT5a expression results from epigenetic gene silencing. In another embodiment epigenetic silencing is promoted by NPM-ALK by activating STAT3. In one embodiment, the distinct pattern and relatively limited extent of STAT5a promoter demethylation after depletion of NPM-ALK and, in one embodiment, STAT3 indicate that demethylation of the specific CpG 'hot spots' within the promoter is sufficient to foster its transcriptional activation. In another embodiment, NPM-ALK utilizes other factors, or mechanisms, to methylate certain areas of the STAT5a promoter.

Accordingly and in one embodiment, the provided herein is a method of inhibiting epigenetic gene silencing in a cell expressing NPM/ALK, comprising the step of contacting a cell with an effective amount of an agent capable of increasing the amount of a Stat5a protein or its functional tumor suppressor analog in a cell.

In another embodiment, provided herein is a composition for inhibiting epigenetic gene silencing, comprising a Stat5a protein or a functional analog thereof, or an agent capable of increasing an mount of Stat5a protein or its analog in the cell, or a combination thereof.

In another embodiment, provided herein is are methods and compositions for treating malignancies expressing oncogenic kinase in a subject, comprising the step of administering to the subject a composition comprising an agent capable of increasing the amount of Stat5a protein or its analog in the cell.

In another embodiment, provided herein is a method of treating malignancies expressing chimeric tyrosine kinase in a subject, comprising the step of administering to the subject a composition comprising an agent capable of increasing the mount of Stat5a protein or its analog in the cell.

In one embodiment, provided herein is a method of treating a proliferative disease in a subject, comprising the step of contacting the subject with a therapeutically effective amount of a composition comprising Stat5a or its mRNA, thereby suppressing tumor proliferation.

In another embodiment, provided herein is a method of preventing, inhibiting or suppressing epigenetically silencing the transcriptional expression of a tumor suppressor in a subject, comprising the step of contacting the subject with a therapeutically effective amount of a composition comprising Stat5a or its mRNA, thereby preventing, inhibiting or suppressing epigenetically silencing the transcriptional expression of a tumor suppressor gene.

In one embodiment, provided herein is a method of treating, inhibiting or suppressing, or ameliorating symptoms associated with a T-cell lymphoma in a subject, comprising the step of administering to the subject a therapeutically effective amount of a composition comprising an agent capable of increasing the expression or function of Stat5a protein or its analog thereby treating, inhibiting or suppressing, or ameliorating symptoms associated with T-cell lymphoma in the subject.

In another embodiment, provided herein is a method of providing a diagnosis for the presence of a malignancy associated with expression of chimeric tyrosine kinase in a subject, comprising the step of: obtaining a t-cell from the subject, analyzing the expression level of: Stat5a, Stat3, NPM/ALK or their combination; and comparing the expression level with a standard.

In one embodiment, provided herein is a method of providing a prognosis for the severity of a malignancy associated with expression of chimeric tyrosine kinase in a subject, comprising the step of: obtaining a T-cell from the subject, analyzing the expression level of: Stat5a, Stat3, NPM/ALK or their combination; and comparing the expression level with a standard.

In another embodiment, provided herein is a method of evaluating the effectiveness of a treatment regimen for a malignancy associated with expression of chimeric tyrosine kinase, comprising the step of: obtaining a T-cell from the subject; analyzing the expression level of: Stat5a, Stat3, NPM/ALK or their combination; and comparing the expression level with a standard.

In another embodiment, provided herein are methods and compositions for decreasing NPM/ALK content in a cell, comprising the step of contacting a cell expressing NPM/ALK with an effective amount of an agent capable of increasing the amount of Stat5a. In another embodiment, NPM/ALK is the fusion protein nucleophosmin-anaplastic lymphoma kinase. In another embodiment, between 20% and 70% of patients with anaplastic large cell lymphoma harbor the balanced chromosomal rearrangement t(2;5)(p23; q35), which results in the generation of NPM/ALK. In another embodiment, NPM/ALK and several other chimeric forms of ALK induce malignant cell transformation.

In one embodiment, provided herein is a method of decreasing NPM/ALK, or another oncogenic-kinase content in a cell, comprising the step of contacting a cell expressing NPM/ALK or another oncogenic-kinase, with an effective amount of an agent capable of increasing the amount of Stat5a or its functional analog, thereby down-regulating the kinase gene expression in the cell. In another embodiment, oncogenic kinase refers to a protein which contributes to malignant cell transformation (carcinogenesis). in another embodiment, kinases become oncogenic by chromosomal translocation, point mutation, and/or persistent activation by protein upstream of them in the cell signaling pathways. The oncogenic kinases include in certain embodiments, both tyrosine and serine/treonine kinases. This include in one embodiment NPM/ALK or in another embodiment, other chimeric forms of ALK, BCR/ABL, ALK with activating point mutations, FLT3 with internal tandem repeat or point mutations, RAS, RAF, mTOR or others in other discrete embodiments of oncogenic kinases treated or diagnosed using the methods described herein.

In another embodiment, ALK is most closely related to the gene LTK (leukocyte tyrosine kinase). In another embodiment, ALK is a large, glycosylated, single chain transmembrane receptor tyrosine kinase and a member of the insulin receptor family. In another embodiment, ALK plays an important role in the normal development and function of the nervous system. In another embodiment, the absence of ALK protein in normal hematopoietic cells means that the expression of ALK in neoplastic cells can be regarded as a clonal tumor marker.

In another embodiment, NPM (known in certain embodiments as NPM1, B23, or numatrin and are used herein interchangeably) is an RNA-binding nucleolar phosphoprotein which is ubiquitously expressed. In another embodiment, NPM cell cycle-dependent functions include the shuttling of ribonucleoproteins between the nucleolus and cytoplasm to the ribosomes.

In another embodiment, NPM-ALK mRNA fusion product is a result of genomic rearrangement involving NPM1 and ALK genes. In another embodiment, the 80 kDa fusion protein NPM-ALK is a constitutively active tyrosine kinase.

In another embodiment, NPM-ALK is localized within both the cytoplasmic and nuclear compartments of the cell. In another embodiment, malignant transformation by NPM-ALK does not involve the alteration of normal NPM functions, but absolutely requires the activated kinase function of ALK. In another embodiment, the NPM-ALK gene fusion are: (1) the ectopic expression of ALK in lymphoid cells, driven by the strong NPM promoter; (2) the constitutive phospho-transferase activity with the NPM moiety serving as an activating sequence; and (3) signaling through various known molecules such as STAT3 and PI3K kinase.

In another embodiment, the invention provides at the molecular cytogenetic level, fluorescence in situ hybridization (FISH) using specific fluorochrome-labeled probes permits detection of the NPM-ALK fusion in both metaphase and interphase cells. In another embodiment, the invention provides an extension of the FISH technique and combination of simultaneous immunophenotyping and interphase cytogenetics, termed FICTION (for fluorescence immunophenotyping and interphase cytogenetics as a tool for investigation of neoplasms).

In another embodiment, the invention provides NPM and/or ALK probes for Southern blot detection of the NPM-ALK fusion. In another embodiment, the invention provides that detection is by the so-called long-range, genomic DNA PCR. In another embodiment, the invention provides that the consistency of the NPM-ALK rearrangement provides the basis for the highly sensitive and specific gene fusion detection by RT-PCR. In another embodiment, the invention provides that RT-PCR is used either in its single step or nested version. Commonly, oligonucleotide primers specific for the NPM-ALK transcript and a primer pair derived from the ubiquitously expressed NPM gene as a control for reverse transcription and amplification are used.

In another embodiment, the invention provides that the NPM-ALK product is specifically detected by hybridization with an end-labeled oligonucleotide homologous to sequences spanning the fusion junction. In another embodiment, the invention provides that isotopic RNA in situ hybridization (RISH) uses 35S-labeled single-stranded RNA probes specific for ALK or NPM sequences. In another embodiment, the invention provides that various antibodies demonstrate of the NPM-ALK fusion at the protein level in both frozen specimens and specimens fixed with formalin or other fixative. In another embodiment, the invention provides that a rabbit polyclonal anti-ALK antibody termed p80, which and/or the polyclonal antibody ALK11 are used for detection. In another embodiment, the invention provides that anti-ALK reagents are ALK1 and ALKc (reacting with different epitopes of ALK). In another embodiment, the invention provides that monoclonal antibodies (McAbs) NA24 and NPMa against the N-terminal portion of NPM (present in NPM-ALK, NPM-MLF1, NPM-RARA) and McAb NPMc against the C-terminal side of NPM (present only in wild-type NPM) are used.

In another embodiment, the invention provides that aberrant ALK expression is critical in the definition of several malignancies, such as anaplastic large cell lymphoma (ALCL) as a disease entity and that the inclusion of this genetic marker as a diagnostic criterion further refines this heterogeneous category, a situation which may have prognostic implications. In another embodiment, the invention provides that the definition of ALK lymphoma on the basis of the ALK protein expression has the great advantage that it is not subject to the problem of identification which would be caused by morphological review alone.

In another embodiment, epigenetic gene silencing refers to nonmutational gene inactivation that can be faithfully propagated from precursor cells to clones of daughter cells. In another embodiment, the addition of methyl groups to cytosine residues in CpG dinucleotides in DNA is a biochemical modification that meets this requirement.

In another embodiment, the mammalian cytosine DNA methyltransferase is encoded by the DNMT1 gene. In another embodiment, this enzyme is able to propagate DNA methylation patterns to daughter strands at each S-phase. In another embodiment, the regulatory domain is targeting of DNMT1 to foci of DNA replication in the nucleus.

In another embodiment, creation of methylation patterns de novo is critical to epigenetic gene silencing in cancer. In another embodiment, the DNMT1 enzyme comprises de novo methylating activity. In another embodiment, 2 additional functional methyltransferases, DNMT3A and DNMT3B exhibit de novo methylating activity both in vitro and in vivo. In another embodiment, DNMT3B is hyperexpressed, at least at the mRNA level, in some human cancers.

In another embodiment, gene silencing by DNA methylation and methyl-DNA binding by capping proteins coupled to histone deacetylation or other modification that fosters gene silencing. In another embodiment, DNA methylation silences genes by interfering with sequence specific binding of positive transcription factors or by producing more general effects on chromatin. In another embodiment, hindrance of transcription by DNA methylation is mediated by general methyl-DNA binding proteins such as methyl CpG binding protein 2 (MeCP2). In another embodiment, epigenetic gene silencing comprises CpG methylation and a second, synergistic epigenetic modification, histone deacetylation on lysine residues. In another embodiment, deacetylation of histones causes an increase in the positive charge of these proteins. In another embodiment, this modification increases the histone's avidity for DNA or for other histones. In another embodiment, the compaction of the chromatin may block access of transcription factors to the DNA or constrain the movement of RNA polymerase.

Accordingly and on one embodiment, provided herein is a method of providing a diagnosis for the presence of a malignancy associated with expression of chimeric tyrosine kinase, or evaluating a treatment effectiveness in a subject, comprising the step of: obtaining a NPM/ALK expressing T-cell from the subject, analyzing the degree of methylation in the CpG island within the Stat5a gene promoter region; and comparing the degree of methylation with a standard taken from another subject.

In another embodiment, provided herein is a method of evaluating the progress of a treatment using 5-aza in a subject, or whether the subject will benefit from a therapy using 5'-aza, comprising the step of obtaining a NPM/ALK expressing T-cell from the subject, analyzing the degree of methylation in the CpG island within the Stat5a gene promoter region; and comparing the degree of methylation with a standard taken from another subject, wherein the standard is taken from another subject or pool of subject that are healthy in one embodiment, or in remission in another embodiment or which are correctly diagnosed with a disease for which the 5'-aza is used for the treatment; and comparing the degree of methylation to that of the standard as a function of time in one embodiment, or treatment modality, dosage, and the like in other discrete embodiments.

The skilled artisan would readily recognize that monitoring the degree of methylation could be done according to methods known in the art. Accordingly and in one embodiment, provided herein is a method of providing a diagnosis for the presence of a malignancy associated with expression of oncogenic kinase, or evaluating a treatment effectiveness in a subject, comprising the step of: obtaining a suspected biological sample from the subject, analyzing the degree of methylation within a promoter or an enhancer region of a gene encoding Stat5a or its functional analog; and comparing the degree of methylation with a standard taken from another subject.

In one embodiment, the term "enhancer domain" refers to a cis-acting transcriptional regulatory element (cis-element), which confers an aspect of the overall modulation of gene expression. An enhancer domain functions in another embodiment to bind transcription factors, or trans-acting protein factors that regulate transcription. Some enhancer domains bind more than one transcription factor, and transcription factors may interact with different affinities with more than one enhancer domain Enhancer domains are identified in certain embodiments, by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from regulatory elements that include such elements, and they can be synthesized with additional flanking nucleotides that contain useful restriction enzyme sites to facilitate subsequence manipulation. In one embodiment, the degree of methylation analyzed using the methods described herein, provide prognosis or diagnosis for the presence, severity or reaction to treatment when the enhancer analyzed is a Stat5a or its functional analog are used.

In one embodiment, the term "promoter" refers to a polynucleotide molecule that is involved in recognition and binding of RNA polymerase II and other proteins such as transcription factors (trans-acting protein factors that regulate transcription) to initiate transcription of an operably linked gene. A promoter may be isolated in certain embodiments, from the 5' untranslated region (5' UTR) of a genomic copy of a gene, such as the Stat5a gene. Promoters are defined in certain embodiments, by their temporal, spatial, or developmental expression pattern. In one embodiment, the degree of methylation analyzed using the methods described herein, provide prognosis or diagnosis for the presence, severity or reaction to treatment when the promoter analyzed for the dfgeree of methylation, is a Stat5a promoter or its functional analog are used.

In another embodiment, MeCP2 physically interacts with the transcriptional corepressor protein Sin3A, and in so doing recruits a histone deacetylase (HDAC) to chromatin that contains methylated DNA.

In another embodiment, the agent is capable of increasing expression of Stat5a or its functional analog. In another embodiment, Stat5a is a transcription factor and tumor suppressor. In another embodiment, growth hormones, growth factors, and cytokines induce Stat5a expression. In another embodiment, estrogen induces Stat5a expression. In another embodiment, progesterone induces Stat5a expression. In another embodiment, interleukin-3 (IL-3) induces Stat5a expression. In another embodiment, stem cell factor (SCF) induces Stat5 expression. In another embodiment, the endogenous ecotropic murine leukemia virus, i.e., SL/Kh virus integration-1 (Svi1), induces Stat5a expression. In another embodiment, retrovirus or lentivirus integration or transfection induces Stat5a expression. In another embodiment, transfection of cells with a vector comprising Stat5a induces Stat5a expression. In another embodiment, transfection of cells with a vector comprising Stat5a under the control of a viral promoter induces Stat5a expression. In another embodiment, transfection of cells with a vector comprising Stat5a under the control of an inducible promoter induces Stat5a expression. In another embodiment, transfection of cells with a vector comprising Stat5a under the control of a constitutively active promoter induces Stat5a expression.

In another embodiment, the agent is Stat5a cDNA. In another embodiment, the agent is Stat5a mRNA. In another embodiment, STAT5a mRNA comprises the following nucleic acid sequence:

```
                                                        (SEQ.ID NO: 1)
5'-CAGACAGGATATTCACTGCTGTGGCAAGGCCTGTAGAGAGTTTCGAAGTTAGGAGGA

CTCAAGACGGTCCCTCCCTGGACTTTTCTGAAGGGGCTCAAAAGATGACACGCGCCAG

AGCTGGAAGGCGTCGCCAATTGGTCCAACTTTTCCCTCCTCCCTTTTTGCGGATGAGAA

AAACTGAGGCCCAGGTTTGGGATTTCCAGAGCCCGGGATTTCCCGGCAACGCCGACAA

CCACATTCCCCCGGCTATTCTGACCCGCCCCGGTTCCGGGACGCTCCCTGGGAGCCGC

CGCCGAGGGCCTGCTGGGACTCCCGGGGACCCCGCCGTCGGGGCAGCCCCCACGCCC

GGCGCCGCCCGCCGGAACGGCGCCGCTGTTGCGCACTTGCAGGGGAGCCGGCGACTG

AGGGCGAGGCAGGGAGGGAGCAAGCGGGGCTGGGAGGGCTGCTGGCGCGGGCTCGC

CGGCTGTGTATGGTCTATCGCAGGCAGCTGACCTTTGAGGAGGAAATCGCTGCTCTCC

GCTCCTTCCTGTAGTAACAGCCGCCGCTGCCGCCGCCGCCAGGAACCCCGGCCGGGAG

CGAGAGCCGCGGGCGCAGAGCCGGCCCGGCTGCCGGACGGTGCGGCCCCACCAGGT

GAACGGCCATGGCGGGCTGGATCCAGGCCCAGCAGCTGCAGGGAGACGCGCTGCGCC

AGATGCAGGTGCTGTACGGCCAGCACTTCCCCATCGAGGTCCGGCACTACTTGGCCCA

GTGGATTGAGAGCCAGCCATGGGATGCCATTGACTTGGACAATCCCCAGGACAGAGC

CCAAGCCACCCAGCTCCTGGAGGGCCTGGTGCAGGAGCTGCAGAAGAAGGCGGAGCA

CCAGGTGGGGAAGATGGGTTTTTACTGAAGATCAAGCTGGGGCACTACGCCACGCA

GCTCCAGAAAACATATGACCGCTGCCCCCTGGAGCTGGTCCGCTGCATCCGGCACATT

CTGTACAATGAACAGAGGCTGGTCCGAGAAGCCAACAATTGCAGCTCTCCGGCTGGG

ATCCTGGTTGACGCCATGTCCCAGAAGCACCTTCAGATCAACCAGACATTTGAGGAGC
```

-continued

```
TGCGACTGGTCACGCAGGACACAGAGAATGAGCTGAAGAAACTGCAGCAGACTCAGG
AGTACTTCATCATCCAGTACCAGGAGAGCCTGAGGATCCAAGCTCAGTTTGCCCAGCT
GGCCCAGCTGAGCCCCCAGGAGCGTCTGAGCCGGGAGACGGCCCTCCAGCAGAAGCA
GGTGTCTCTGGAGGCCTGGTTGCAGCGTGAGGCACAGACACTGCAGCAGTACCGCGTG
GAGCTGGCCGAGAAGCACCAGAAGACCCTGCAGCTGCTGCGGAAGCAGCAGACCATC
ATCCTGGATGACGAGCTGATCCAGTGGAAGCGGCGGCAGCAGCTGGCCGGGAACGGC
GGGCCCCCCGAGGGCAGCCTGGACGTGCTACAGTCCTGGTGTGAGAAGTTGGCCGAG
ATCATCTGGCAGAACCGGCAGCAGATCCGCAGGGCTGAGCACCTCTGCCAGCAGCTG
CCCATCCCCGGCCCAGTGGAGGAGATGCTGGCCGAGGTCAACGCCACCATCACGGAC
ATTATCTCAGCCCTGGTGACCAGCACATTCATCATTGAGAAGCAGCCTCCTCAGGTCC
TGAAGACCCAGACCAAGTTTGCAGCCACCGTACGCCTGCTGGTGGGCGGGAAGCTGA
ACGTGCACATGAATCCCCCCCAGGTGAAGGCCACCATCATCAGTGAGCAGCAGGCCA
AGTCTCTGCTTAAAAATGAGAACACCCGCAACGAGTGCAGTGGTGAGATCCTGAACA
ACTGCTGCGTGATGGAGTACCACCAAGCCACGGGCACCCTCAGTGCCCACTTCAGGAA
CATGTCACTGAAGAGGATCAAGCGTGCTGACCGGCGGGGTGCAGAGTCCGTGACAGA
GGAGAAGTTCACAGTCCTGTTTGAGTCTCAGTTCAGTGTTGGCAGCAATGAGCTTGTG
TTCCAGGTGAAGACTCTGTCCCTACCTGTGGTTGTCATCGTCCACGGCAGCCAGGACC
ACAATGCCACGGCTACTGTGCTGTGGGACAATGCCTTTGCTGAGCCGGGCAGGGTGCC
ATTTGCCGTGCCTGACAAAGTGCTGTGGCCGCAGCTGTGTGAGGCGCTCAACATGAAA
TTCAAGGCCGAAGTGCAGAGCAACCGGGGCCTGACCAAGGAGAACCTCGTGTTCCTG
GCGCAGAAACTGTTCAACAACAGCAGCAGCCACCTGGAGGACTACAGTGGCCTGTCC
GTGTCCTGGTCCCAGTTCAACAGGGAGAACTTGCCGGGCTGGAACTACACCTTCTGGC
AGTGGTTTGACGGGGTGATGGAGGTGTTGAAGAAGCACCACAAGCCCCACTGGAATG
ATGGGGCCATCCTAGGTTTTGTGAATAAGCAACAGGCCCACGACCTGCTCATCAACAA
GCCCGACGGGACCTTCTTGTTGCGCTTTAGTGACTCAGAAATCGGGGGCATCACCATC
GCCTGGAAGTTTGACTCCCCGGAACGCAACCTGTGGAACCTGAAACCATTCACCACGC
GGGATTTCTCCATCAGGTCCCTGGCTGACCGGCTGGGGGACCTGAGCTATCTCATCTA
TGTGTTTCCTGACCGCCCCAAGGATGAGGTCTTCTCCAAGTACTACACTCCTGTGCTGG
CTAAAGCTGTTGATGGATATGTGAAACCACAGATCAAGCAAGTGGTCCCTGAGTTTGT
GAATGCATCTGCAGATGCTGGGGGCAGCAGCGCCACGTACATGGACCAGGCCCCCTC
CCCAGCTGTGTGCCCCCAGGCTCCCTATAACATGTACCCACAGAACCCTGACCATGTA
CTCGATCAGGATGGAGAATTCGACCTGGATGAGACCATGGATGTGGCCAGGCACGTG
GAGGAACTCTTACGCCGACCAATGGACAGTCTTGACTCCCGCCTCTCGCCCCCTGCCG
GTCTTTTCACCTCTGCCAGAGGCTCCCTCTCATGAATGTTTGAATCCCACGCTTCTCTTT
GGAAACAATATGCAATGTGAAGCGGTCGTGTTGTGAGTTTAGTAAGGTTGTGTACACT
GACACCTTTGCAGGCATGCATGTGCTTGTGTGTGTGTGTGTGTGTGTCCTTGTGCAT
GAGCTACGCCTGCCTCCCCTGTGCAGTCCTGGGATGTGGCTGCAGCAGCGGTGGCCTC
TTTTCAGATCATGGCATCCAAGAGTGCGCCGAGTCTGTCTCTGTCATGGTAGAGACCG
AGCCTCTGTCACTGCAGGCACTCAATGCAGCCAGACCTATTCCTCCTGGGCCCCTCATC
TGCTCAGCAGCTATTTGAATGAGATGATTCAGAAGGGGAGGGGAGACAGGTAACGTC
```

```
-continued
TGTAAGCTGAAGTTTCACTCCGGAGTGAGAAGCTTTGCCCTCCTAAGAGAGAGAGACA

GAGAGACAGAGAGAGAGAAAGAGAGAGTGTGTGGGTCTATGTAAATGCATCTGTCCT

CATGTGTTGATGTAACCGATTCATCTCTCAGAAGGGAGGCTGGGGGTTCATTTTCGAG

TAGTATTTTATACTTTAGTGAACGTGGACTCCAGACTCTCTGTGAACCCTATGAGAGCG

CGTCTGGGCCCGGCCATGTCCTTAGCACAGGGGGGCCGCCGGTTTGAGTGAGGGTTTC

TGAGCTGCTCTGAATTAGTCCTTGCTTGGCTGCTTGGCCTTGGGCTTCATTCAAGTCTA

TGATGCTGTTGCCCACGTTTCCCGGGATATATATTCTCTCCCCTCCGTTGGGCCCCAGC

CTTCTTTGCTTGCCTCTCTGTTTGTAACCTTGTCGACAAAGAGGTAGAAAAGATTGGGT

CTAGGATATGGTGGGTGGACAGGGGCCCCGGGACTTGGAGGGTTGGTCCTCTTGCCTC

CTGGAAAAAACAAAAACAAAAAACTGCAGTGAAAGACAAGCTGCAAATCAGCCATGT

GCTGCGTGCCTGTGGAATCTGGAGTGAGGGGTAAAAGCTGATCTGGTTTGACTCCGCT

GGAGGTGGGGCCTGGAGCAGGCCTTGCGCTGTTGCGTAACTGGCTGTGTTCTGGTGAG

GCCTTGCTCCCAACCCCACACGCTCCTCCCTCTGAGGCTGTAGGACTCGCAGTCAGGG

GCAGCTGACCATGGAAGATTGAGAGCCCAAGGTTTAAACTTCTCTGAAGGGAGGTGG

GGATGAGAAGAGGGGTTTTTTTGTACTTTGTACAAAGACCACACATTTGTGTAAACAG

TGTTTTGGAATAAAATATTTTTTTCAT-'3.
```

In another embodiment, STAT5a mRNA comprises the nucleic acid sequence represented by gene bank accession number: NM_003152. In another embodiment, a STAT5a mRNA or cDNA sequence comprises rat STAT5a mRNA or cDNA sequence. In another embodiment, a STAT5a mRNA or cDNA sequence comprises murine STAT5a mRNA or cDNA sequence. In another embodiment, a STAT5a mRNA or cDNA sequence comprises primate STAT5a mRNA or cDNA sequence. In another embodiment, a STAT5a mRNA or cDNA sequence comprises human STAT5a mRNA or cDNA sequence.

In another embodiment, methods and compositions of the present invention utilize a homologue of a STAT5a mRNA or cDNA sequence (e.g. SEQ ID No: 1). The terms "homology," "homologous," etc, when in reference to any nucleic acid sequence, refer in one embodiment, to a percentage of nucleic acid residues in the candidate sequence that are identical with the residues of a corresponding native gene, after aligning the sequences and introducing gaps, if necessary, to achieve the maximum percent homology, and not considering any conservative substitutions as part of the sequence identity. Methods and computer programs for the alignment are well known in the art.

In another embodiment, STAT5a mRNA or cDNA sequence comprises a sequence that has at least 60% homology to SEQ. ID. NO: 1. In another embodiment, STAT5a mRNA or cDNA sequence comprises a sequence that has at least 65% homology to SEQ. ID. NO: 1. In another embodiment, STAT5a mRNA or cDNA sequence comprises a sequence that has at least 70% homology to SEQ. ID. NO: 1. In another embodiment, STAT5a mRNA or cDNA sequence comprises a sequence that has at least 75% homology to SEQ. ID. NO: 1. In another embodiment, STAT5a mRNA or cDNA sequence comprises a sequence that has at least 80% homology to SEQ. ID. NO: 1. In another embodiment, STAT5a mRNA or cDNA sequence comprises a sequence that has at least 85% homology to SEQ. ID. NO: 1. In another embodiment, STAT5a mRNA or cDNA sequence comprises a sequence that has at least 90% homology to SEQ. ID. NO: 1. In another embodiment, STAT5a mRNA or cDNA sequence comprises a sequence that has at least 95% homology to SEQ. ID. NO: 1. In another embodiment, STAT5a mRNA or cDNA sequence comprises a sequence that has at least 98% homology to SEQ. ID. NO: 1.

In another embodiment, the invention provides further contacting a cell with an additional agent capable of inhibiting the expression or function of methyl CpG binding protein 2 (MeCP2) protein. In another embodiment, the invention provides further contacting a cell with an additional agent capable of inhibiting the expression or function of methyl-CpG binding domain-1 (MBD1). In another embodiment, the invention provides further contacting a cell with an additional agent capable of inhibiting the expression or function of MBD2. In another embodiment, the invention provides further contacting a cell with an additional agent capable of inhibiting the expression or function of MBD3. In another embodiment, the invention provides further contacting a cell with an additional agent capable of inhibiting the expression or function of MBD4.

In another embodiment, the additional agent is a hormone. In another embodiment, the additional agent is a growth factor. In another embodiment, the additional agent is a cytokine receptor stimulator. In another embodiment, the additional agent is an estrogen receptor repressor. In another embodiment, the additional agent is an estrogen receptor inhibitor. In another embodiment, the additional agent is a methyl CpG binding protein antisense molecule. In another embodiment, the additional agent is a methyl DNA binding protein antisense morpholino oligomer. In another embodiment, the additional agent is a methyl CpG binding protein antisense morpholino oligomer. In another embodiment, the additional agent is an antisense morpholino oligomer directed to the translational initiation site for a methyl CpG binding protein. In another embodiment, the additional agent is an antisense morpholino oligomer directed to the translational initiation site for MeCP2. In another embodiment, the additional agent is an antisense morpholino oligomer directed to the translational initiation site for MeCP2beta.

In another embodiment, the additional agent is antisense oligonucleotides comprising a single strand DNA. In another embodiment, the additional agent is antisense oligonucleotides comprising a single strand RNA. In another embodiment, the additional agent is antisense oligonucleotides complementary to the translational initiation site for a methyl DNA binding protein. In another embodiment, the additional agent is antisense oligonucleotides complementary to the translational initiation site for a methyl CpG binding protein. In another embodiment, the additional agent is antisense oligonucleotides complementary to the translational initiation site for MeCP2.

In another embodiment, the additional agent is an aptamer. In another embodiment, the aptamer comprises nucleic acid species that have been engineered through repeated rounds of in vitro selection or equivalently, SELEX (systematic evolution of ligands by exponential enrichment) to bind a methyl CpG binding protein such as MeCP2. In another embodiment, the aptamer is a DNA aptamer. In another embodiment, the aptamer is an RNA aptamer. In another embodiment, the aptamer is a non-modified aptamer. In another embodiment, the aptamer is a 2'-fluorine-substituted pyrimidines modified aptamer. In another embodiment, the aptamer is a polyethylene glycol (PEG) linked modified aptamer. In another embodiment, the aptamer is any modified aptamer known to one of skill in the art. In another embodiment, the additional agent is an aptamer complementary to the translational initiation site for a methyl CpG binding protein. In another embodiment, the additional agent is antisense oligonucleotides complementary to the translational initiation site for MeCP2.

In another embodiment, the additional agent is a peptide aptamer. In another embodiment, a peptide aptamer is designed to interfere between the interactions of a methyl CpG binding protein with other proteins in a cell. In another embodiment, a peptide aptamer is designed to interfere between the interactions of MeCP2 with other proteins in a cell. In another embodiment, the peptide aptamer comprises a variable loop length typically comprising of 10 to 20 amino acids. In another embodiment, the peptide aptamer comprises a protein scaffold. In another embodiment, the peptide aptamer comprises a soluble protein scaffold. In another embodiment, the scaffold is Thioredoxin-A. In another embodiment, the variable loop is inserted within the reducing active site, which is a -Cys-Gly-Pro-Cys-loop in the wild protein, the two cysteins lateral chains being able to form a disulfide bridge. In another embodiment, a peptide aptamer of the invention is selected in a yeast two-hybrid system. In another embodiment, selection of Ligand Regulated Peptide Aptamers (LiRPAs) is carried out by displaying 7 amino acid peptides from a novel scaffold protein based on the trimeric FKBP-rapamycin-FRB structure, interaction between the randomized peptide and target methyl CpG binding protein can be controlled by the small molecule rapamycin or its non-immunosuppressive analogs.

In another embodiment, the additional agent is a ribozyme. In another embodiment, the additional agent is a RNase P ribozyme. In another embodiment, the additional agent is a Leadzyme. In another embodiment, the additional agent is a Hairpin ribozyme. In another embodiment, the additional agent is a Hammerhead ribozyme. In another embodiment, the additional agent is a hepatitis delta virus ribozyme. In another embodiment, the additional agent is a Tetrahymena ribozyme. In another embodiment, the additional agent is a VS ribozyme. In another embodiment, the additional agent is a GlmS ribozyme. In another embodiment, the additional agent comprises siRNA. In another embodiment, the additional agent comprises shRNA. In another embodiment, the additional agent comprises microRNA. In another embodiment, the additional agent comprises RNAi. In another embodiment, the additional agent comprises an antisense agent directed to the translational initiation site for a methyl CpG binding protein. In another embodiment, the additional agent comprises an antisense agent directed to the translational initiation site for MeCP2. In another embodiment, the additional agent comprises a polyamide. In another embodiment, the additional agent comprises a triple-helix-forming agent. In another embodiment, the additional agent comprises a synthetic peptide nucleic acids (PNAs), In another embodiment, the additional agent comprises an agRNA. In another embodiment, the additional agent comprises a LNA/DNA copolymer. In another embodiment, the additional agent comprises a small molecule chemical compound. In another embodiment, the additional agent is specific against a nucleotide sequence encoding MeCP2 protein.

In another embodiment, the agent capable of inhibiting the function of a methyl CpG binding protein such as MeCP2 protein is an antibody or a fragment thereof, specific against a methyl CpG binding protein. In another embodiment, the antibody is a monoclonal antibody. In another embodiment, the antibody is a polyclonal antibody. In another embodiment, the antibodies of the invention comprise a mixture of monoclonal antibodies. In another embodiment, the antibody is a monoclonal single chain variable fragments (scFv) anti-methyl CpG binding protein protein antibody. In another embodiment, the fragment is F(ab')$_2$, F(ab') Fc, scFv fragment or a combination thereof.

In another embodiment, the agent is a DNA methyltransferase (DNMT) inhibitor. In another embodiment, the agent is azacitidine (5-azacytidine; Vidaza®, Pharmion Corp., Boulder, Colo., USA). In another embodiment, the agent is decitabine (5-aza-2'-deoxycytidine; Dacogen™, SuperGen Inc., Dublin, Calif., USA, and MGI Pharma Inc., Bloomington, Minn., USA). In another embodiment, the agent is doxorubicin. In another embodiment, the DNMT inhibitor is MG98. In another embodiment, the DNMT inhibitor is S-adenosyl-homocysteine (SAH) or an analogue thereof. In one embodiment, the analogue is periodate-oxidized adenosine or 3-deazaadenosine. In another embodiment, the DNMT inhibitor is a DNA-based inhibitor such as those described in Bigey, P et al, J. Biol. Chem, 274, 4594-4606, 1999. In another embodiment, the DNMT inhibitor is an antisense nucleotide such as those described in Ramchandani, S et al. Proc Natl, Acad. Sci. USA, 94, 684-689, 1997; Fournel, M et al, J. Biol. Chem., 274, 24250-24256, 1999. In another embodiment, the DNMT inhibitor is any other DNMT inhibitor known in the art Each DNMT inhibitor represents a separate embodiment of the present invention.

In another embodiment, provided herein is a use of an agent or a combination of agents of the invention for the preparation of a pharmaceutical composition for inhibiting epigenetic gene silencing in a cell expressing NPM/ALK. In another embodiment, provided herein is a use of an agent or a combination of agents of the invention for the preparation of a pharmaceutical composition for reducing an extent of epigenetic gene silencing in a cell expressing NPM/ALK. In another embodiment, provided herein is a use of an agent or a combination of agents of the invention for the preparation of a pharmaceutical composition for reducing an extent of epigenetic gene silencing in a cell expressing NPM/ALK.

In another embodiment, a pharmaceutical composition of the invention is administered to a subject in need. In another embodiment, contacting is via oral or parenteral administration or a combination thereof. In another embodiment, a pharmaceutical composition of the invention is administered via oral or parenteral administration. In another embodiment, a pharmaceutical composition of the invention is administered intravenously. In another embodiment, a pharmaceutical composition of the invention is administered intrathecaly. In another embodiment, a pharmaceutical composition of the invention is administered intratumoraly. In another embodiment, a pharmaceutical composition of the invention is administered subcutaneously. In another embodiment, a pharmaceutical composition of the invention is administered intranasaly. In another embodiment, a pharmaceutical composition of the invention is administered intraperitonealy.

In another embodiment, the pharmaceutical compositions are administered orally, and thus is formulated in a form suitable for oral administration, i.e as a solid or a liquid preparation Suitable solid oral formulations include, for example, tablets, capsules, pills, granules, pellets and the like. Suitable liquid oral formulations include solutions, suspensions, dispersions, emulsions, oils and the like. In one embodiment of the present invention, the HDAC inhibitor or DNMT inhibitor is formulated in a capsule. In accordance with this embodiment, the compositions of the present invention comprise, in addition to the HDAC inhibitor or DNMT inhibitor active compound and the inert earner or diluent, a hard gelating capsule.

In another embodiment, the pharmaceutical compositions are administered by intravenous, intraarterial, or intramuscular injection of a liquid preparation. Suitable liquid formulations include solutions, suspensions, dispersions; emulsions, oils and the like. In another embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

In another embodiment, the pharmaceutical compositions are administered topically to body surfaces, and thus are formulated in a form suitable for topical administration. Suitable topical formulations include gels, ointments, creams, lotions, drops and the like.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of the agent or combination of agents over a period of time.

Pharmaceutically acceptable carriers or diluents are well known to those skilled in the art. The carrier or diluent is, in one embodiment, a solid carrier or diluent for solid formulations, a liquid carrier or diluent for liquid formulations, or mixtures thereof.

Solid carriers/diluents include, but are not limited to a gum, a starch (e.g. corn starch, pregeletanized starch), a sugar (e g, lactose, mannilol, sucrose, dextrose), a cellulosic material (e.g. microcrystalline cellulose), an acrylate (e g polymethylacrylate), calcium carbonate, magnesium oxide, talc, or mixtures thereof.

For liquid formulations, pharmaceutically acceptable carriers are aqueous or nonaqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media Examples of oils are those of petroleum, animal, vegetable, or synthetic origin, for example, peanut oil. soybean oil mineral oil, olive oil, sun flower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils Intravenous vehicles include fluid and nutrient replenishes, electrolyte replenishes such as those based on Ringer's dextrose, and the like. Examples are sterile liquids such as water and oils, with or without the addition of a surfactant and other pharmaceutically acceptable adjuvants, In general, water, saline, aqueous dextrose and elated sugar solutions, and glycols such as propylene glycols or polyethylene glycol are preferred liquid carriers, particularly for injectable solutions Examples of oils are those of petroleum, animal, vegetable, or synthetic origin, for example, peanut oil, soybean oil, mineral oil, olive oil, sunflower oil, and fish-liver oil.

In another embodiment, the compositions further comprise binders (e.g acacia, cornstarch, gelatin, caibomei, ethyl cellulose, guar gum, hydroxypropyl cellulose, hydroxypropyl methyl cellulose, povidone), disintegrating s (e.g. cornstarch, potato starch, alginic acid, silicon dioxide, croscarmelose sodium, ciospovidone, guar gum, sodium starch glycolate), buffers (e.g., Tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizers (e.g. glycerol, polyethylene glycerol), anti-oxidants (e.g, ascorbic acid, sodium metabisulfite, butylated hydroxyanisole), stabilizers (e.g hydroxypropyl cellulose, hydroxypropylmethyl cellulose), viscosity increasing s (e.g carbomer, colloidal silicon dioxide, ethyl cellulose, guar gum), sweetners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g diethyl phthalate, triethyl citrate), emulsifiers (e.g carbomer. hydroxypropyl cellulose, sodium lauryl sulfate), polymer coatings (e.g., poloxamers or poloxamines), coating and film forming s (e g ethyl cellulose, acrylates, polymethacrylates) and/or adjuvants In another embodiment, the pharmaceutical compositions provided herein are controlled release compositions. Controlled or sustained release compositions include formulation in lipophilic depots (e.g, fatty acids, waxes, oils). In another embodiment, the composition is an immediate release composition.

In another embodiment, the pharmaceutical composition is delivered in a controlled release system. For example, the composition is administered using intravenous infusion, an implantable osmotic pump, a transdermal patch, liposomes, or other modes of administration.

In another embodiment, polymeric materials can be used. In yet another embodiment, a controlled release system can be placed in proximity to the therapeutic target, thus requiring only a fraction of the systemic dose (e.g. Goodson, in Medical Applications of Controlled Release, supra, vol. 2, pp 1 15-138 (1984). Other controlled release systems are discussed in the review by Langer (Science 249:1527-1533 (1990).

The preparation of pharmaceutical compositions which contain an active component is well understood in the art, for example by mixing, granulating, or tablet-forming processes The active therapeutic ingredient is often mixed with excipients which are pharmaceutically acceptable and compatible with the active ingredient. For oral administration, the agents of the invention or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the agents of the invention or their physiologically tolerated derivatives such as salts, esters, N-oxides, and the like are converted into a solution, suspension, or emulsion, if desired with the substances customary and suitable for this purpose, for example, solubilizers or other.

In another embodiment, the active component is formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, of ferric hydroxides, and such organic bases as isopropylamine, trimethylamine, 2-ethylamino ethanol, histidine, and the like.

In another embodiment, the salts of the agents of the invention are pharmaceutically acceptable salts. Other salts are. In one embodiment, useful in the preparation of the compounds according to the invention or of their pharmaceutically acceptable salts Suitable pharmaceutically acceptable salts of the compounds of this invention include acid addition salts which may. for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In another embodiment, the malignancy is characterized by malignant cells expressing chimeric tyrosine kinase or another oncogenic kinase. In another embodiment, the malignancy is lymphoma. In another embodiment, the malignancy is sarcoma. In another embodiment, the malignancy is leukemia. In another embodiment, the malignancy is carcinoma. In another embodiment, the malignancy is characterized by malignant cells expressing NPM/ALK. In another embodiment, the malignancy is or associated with: adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, Ewings family of tumors (pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, small cell, lymphoma, AIDS-related, lymphoma, central nervous system (primary), lymphoma, cutaneous T-cell, lymphoma, Hodgkin's disease, non-Hodgkin lymphoma, malignant mesothelioma, melanoma, merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, sezary syndrome, skin cancer, cutaneous T-cell lymphoma, skin cancer, kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, or Wilms' tumor.

Accordingly and in one embodiment, the methods and compositions described herein, are effective in the treatment of Chronic myelogenous leukemia (CML), which is a hematological malignancy that is characterized by the chromosome anomaly, t(9;22)(q34;q11). The chromosomal translocation generates in one embodiment a chimeric tyrosine kinase, BCR-ABL chimeric protein, which is pathognomonic of the disease. Accordingly, provided herein is a method of preventing CML in a subject, comprising the step of contacting a cell expressing BCR-ABL with a composition comprise an agent capable of increasing the amount of Stat5a or its functional analog in the cell.

In another embodiment, Congenital (or infantile) fibrosarcoma (CFS) refers to a malignant tumour of fibroblasts that occurs in patients aged two years or younger. In one embodiment a recurrent t(12;15)(p13;q25) rearrangement in CFS underlies the distinctive biological properties of this tumour. In one embodiment, the rearrangement fuses the ETV6 (known in another embodiment as TEL) gene from 12p13 with the 15q25 NTRK3 neurotrophin-3 receptor gene (known as TRKC in certain embodiments). In one embodiment ETV6-NTRK3 fusion transcripts encode the helix-loop-helix (HLH) protein dimerization domain of ETV6 fused to the protein tyrosine kinase (PTK) domain of NTRK3. In another embodiment a chimeric PTK is expressed in CFS contributing in one embodiment to oncogenesis by dysregulation of NTRK3 signal transduction pathways. Accordingly and in one embodiment, the methods and compositions described herein, are effective in preventing CFS in a subject, comprising the step of contacting a cell expressing ETV6-NTRK3 with a composition comprise an agent capable of increasing the amount of Stat5a in the cell.

In one embodiment oligomeric antisense compounds, particularly oligonucleotides, are used in the photocleavable hairpin oligonucleotide constructs provided herein. This is accomplished by providing antisense compounds which specifically hybridize with one or more sense ODN's as herein. As used herein, the terms "target nucleic acid" refers in one embodiment to RNA (including pre-mRNA and mRNA) transcribed from a DNA, and also cDNA derived from such RNA. The specific hybridization of an oligomeric compound with its target nucleic acid interferes in another embodiment, with the normal function of the nucleic acid. The modulation of function of a target nucleic acid by compounds which specifically hybridize to it, is referred to in one embodiment as "antisense". In one embodiment, the functions of DNA to be interfered with using the antisense oligonucleotides described herein, such as Stat3 or MeCP2 and their combination in one embodiment (see FIG. 12), which are used in the methods and compositions described herein, include replication and transcription. In another embodiment, functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the function of the target nucleic acid. In one embodiment, inhibition of gene expression is preferred and mRNA is a preferred target. In one embodiment, since many genes (including NPM, MeCP2 or Stat3) have multiple transcripts, "inhibition" also includes an alteration in the ratio between gene products, such as alteration of mRNA splice products.

In one embodiment, specific nucleic acids are targeted for antisense. "Targeting" an antisense compound to a particular nucleic acid, in one embodiment, is a multi-step process. The process usually begins with the identification of a nucleic acid sequence whose function is to be inhibited. This may be, for example, a cellular gene (or mRNA transcribed from the gene) whose expression is associated with a particular disorder or disease state, or a nucleic acid molecule from an infectious agent. The targeting process also includes in another embodiment, determination of a site or sites within this gene for the antisense interaction to occur such that the desired effect, e g, inhibition of expression of the protein such as chordin, will result. In one embodiment, an intragenic site is the region encompassing the translation initiation or termination codon of the open reading frame (ORF) of the gene. Since, the translation initiation codon is in one embodiment 5'-AUG (in transcribed mRNA molecules; 5'-ATG in the corresponding DNA molecule), the translation initiation codon is referred to in one embodiment as the "AUG codon," the "start codon" or the "AUG start codon". In another embodiment, a minority of genes have a translation initiation codon having the RNA sequence 5'-GUG, 5'-UUG or 5'-CUG, and 5'-AUA, 5'-ACG and 5'-CUG and have been shown to function in vivo. Thus, the terms "translation initiation codon" and "start codon" encompasses in other embodiments, many codon sequences, even though the initiator amino acid in each instance is typically methionine (in eukaryotes) or formylmethionine (in prokaryotes).

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be target regions in one embodiment, and are particularly useful in situations where aberrant splicing is implicated in disease, or where an overproduction of a particular mRNA splice product is implicated in disease in other embodiment, such as symptoms associated with HSV infection. Aberrant fusion junctions due to rearrangements or deletions are also preferred targets. In one embodiment, introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect. In one embodiment, the term "hybridization" refers to hydrogen bonding, which may be Watson-Crick, Hoogsteen or reversed Hoogsteen hydrogen bonding, between complementary nucleoside or nucleotide bases. In one embodiment, adenine and thymine are complementary nucleotide bases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are used in one embodiment, as research reagents and diagnostics. In another embodiment, antisense oligonucleotides, which are able to inhibit gene function, with extreme specificity, are used by those of ordinary skill to elucidate the function of particular genes. Antisense compounds are used in another embodiment, to distinguish between functions of various members of a biological pathway. Antisense modulation has, in one embodiment of the agents described in the methods and compositions described herein, been harnessed for research use.

In one embodiment, the specificity and sensitivity of antisense agents described herein, is also harnessed for therapeutic uses. Antisense oligonucleotides are employed in one embodiment, as therapeutic moieties in the treatment of disease states in animals and man, such as, in another embodiment, those associated with cancer. In one embodiment, antisense oligonucleotides are safely and effectively administered to humans. In one embodiment oligonucleotides are useful therapeutic modalities that can be configured to be useful in treatment regimes of cells, tissues and animals, especially humans. Such configuration include inter-alia making the conjugates and compositions described herein, target NPM, Stat3 or MeCP2 and their combination and to be nuclease-resistant inside lymphoma cells. In one embodiment, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, the term "locked nucleic acid" (LNA) refers to a synthetic nucleic acid analogue, incorporating "internally bridged" nucleoside analogues. Synthesis of LNA, and properties thereof, have been described by a number of authors: Nielsen et al, (1997 J. Chem. Soc. Perkin Trans. 1, 3423); Koshkin et al, (1998 Tetrahedron Letters 39, 4381); Singh & Wengel (1998 Chem. Commun 1247); and Singh et al, (1998 Chem. Commun 455). As with PNA, LNA exhibits greater thermal stability when paired with DNA, than do conventional DNA/DNA heteroduplexes. In one embodiment, LNA can be joined to DNA molecules by conventional techniques. Therefore, in one embodiment, LNA is to be preferred over PNA, for use in the agents of the methods and compositions described herein.

In one embodiment, the antisense oligonucleotide (asODN) used in the methods and compositions described herein, is between about 5 and 50 nucleotides in length. In another embodiment, the antisense oligonucleotide is between 5 and 10 nucleotides in length, or in another embodiment, the antisense oligonucleotide is between 5 and 15 nucleotides in length, or in another embodiment, the antisense oligonucleotide is between 5 and 20 nucleotides in length, or in another embodiment, the antisense oligonucleotide is between 5 and 25 nucleotides in length, or in another embodiment, the antisense oligonucleotide is between 5 and 30 nucleotides in length, or in another embodiment, the antisense oligonucleotide is between 5 and 35 nucleotides in length, or in another embodiment, the antisense oligonucleotide is between 5 and 40 nucleotides in length, or in another embodiment, the antisense oligonucleotide is between 5 and 45 nucleotides in length, or in another embodiment, the antisense oligonucleotide is between 5 and 49 nucleotides in length. In one embodiment, the antisense oligonucleotide (asODN) used in the methods and compositions described herein, is between about 10 and 20 nucleotides in length. In another embodiment, the antisense oligonucleotide is between 15 and 25 nucleotides in length, or in another embodiment, the antisense oligonucleotide is between 20 and 30 nucleotides in length, or in another embodiment, the antisense oligonucleotide is between 25 and 35 nucleotides in length.

In another embodiment, the 5' end of the antisense oligonucleotide and the 3' end of the sense oligonucleotide used in the methods and compositions described herein, each contain a region that is not complementary to the opposite strand. In one embodiment, having a non-complementary region in the sense or antisense ODNs used in the methods and compositions described herein, which is no less than 5 nucleotides in another embodiment, allows the design of the desired stability of the conjugate, by controlling the length of the complementary oligonucleotides. In one embodiment, the methods and compositions described herein, allow for the use of a 30-40 mer asODN with a much shorter sODN, thereby controlling the strength of interactions in the conjugate.

In another embodiment, the antisense or sense oligonucleotide used in the methods and compositions described herein, is a DNA peptide nucleic acid (PNA), phosphorothioate DNA, phosphorodithioate DNA, phosphoramidate DNA, amide-linked DNA, MMI-linked DNA, 2'-O-methyl RNA, alpha-DNA, methylphosphonate DNA, 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, anhydrohexitol DNA, C-5 substituted pyrimidine nucleoside, C-7 substituted 7-deazapurine nucleoside, inosine nucleoside phosphorodiamidate morpholino oligonucleotide (PMO), a locked nucleic acid (LNA) or diaminopurine nucleoside.

In one embodiment, the term "peptide nucleic acid (PNA)" refers to a polyglycine backbone, having purine and pyrimidine bases linked thereto by methylene carbonyl bonds. In one embodiment, since the backbone of PNA does not have any charged phosphate groups, the binding between asPNA/DNA strands used in the methods and compositions described herein, is stronger than between DNA/DNA strands due to the lack of electrostatic repulsion. In another embodiment, ncPNA does have alternating peptide and negatively charged phosphate groups. The negative charge makes the ncPNA more soluble than PNA.

Since, sDNA may prove to be toxic in certain applications, 2'-0Me sRNA may be selected as the blocking strand. In certain embodiments, the choice of sODN and asODN are optimized for the application for which they are used, and the skilled practitioner would readily recognize that experimentation as to the choice of reactive group (asODN) size and composition and the blocking group (sODN) size and composition, to optimize the functionality of the conjugate are well within the purview of due experimentation.

In another embodiment, locked nucleic acid (LNA) refers to a modified RNA nucleotide. Ribose moiety of LNA nucleotide is modified in one embodiment, with an extra bridge connecting 2' and 4' carbons. The bridge "locks" the ribose in the 3'-endo structural conformation, which is found in one embodiment, in A-form of DNA or RNA. LNA nucleotides may be mixed with DNA or RNA bases in the oligonucleotide in certain embodiments. The LNA oligonucleotides provided herein enhance base stacking and backbone pre-organization, which increases significantly the thermal stability (melting temperature) of the oligonucleotide conjugate.

In one embodiment, the term phosphorodiamidate morpholino oligonucleotide (PMO) refers to a synthetic polymorpholino backbone, to which nucleotide bases are linked through phosphorodiamidate groups. Like PNAs, PMOs do not have any charged phosphate groups, making the binding between asPMO/DNA strands used in the methods and compositions described herein, stronger than between DNA/DNA strands due to the lack of electrostatic repulsion. In certain embodiments, ncPNAs (unlike PMOs) do have charged phosphate groups, which is important for some applications.

In one embodiment, minor groove-binding N-methylpyrrole (Py) and N-methylimidazole (Im) polyamides (peptides) uniquely recognize each of the four Watson-Crick base pairs. Antiparallel pairing of imidazole with pyrrole (Im/Py) recognizes in one embodiment, a G-C base pair, whereas in another embodiment, a Py/Py pair recognizes either an A-T or T-A base pair. The binding constant and sequence-specificity of the Py-Im hairpin polyamides are similar to that of a transcription factor. Therefore, many genes are silenced in other embodiments, by competitive binding of Py-Im hairpin polyamides to their regulatory sequences. Gene expression is controlled in one embodiment, by a combination of multiple common transcription factors. In one embodiment, inhibition of gene expression through the binding of Py-Im polyamides to regulatory sequences is unique to a specific gene, and contains part of the recognition sequence of the transcription factor together with the unique flanking sequences. In another embodiment, targeting Py-Im polyamide to the coding region is more straightforward when selecting a unique sequence.

In one embodiment, a homopyrimidine DNA strand (triplex forming oligonucleotide, TFO) can bind to a homopurine/homopyrimide DNA duplex in the major groove by forming Hoogsteen base pairs with the homopurine strand. The Hoogsteen base pairing scheme mediates sequence specific recognition of the double stranded DNA by the TFO where in one embodiment, an AT base pair is recognized by a T; and a GC base pair by a C that is protonated at $N3^+$. In another embodiment, homopurine strands specifically form a DNA triplex in which the AT base pair is contacted by an A; and the GC base pair by a G. In one embodiment, the protected asODN component used in the conjugates and methods described herein, is a triplex forming oligonucleotide.

In one embodiment, the term "TFO" or "triplex forming oligonucleotide" refers to the synthetic oligonucleotides of the present invention which are capable of forming a triple helix by binding in the major groove with a duplex DNA structure.

In another embodiment, the term "bases" refers to both the deoxyribonucleic acids and ribonucleic acids. The following abbreviations are used, "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill in this art would readily recognize that these bases may be modified or derivatized to optimize the methods described herein, without changing the scope of the invention.

In one embodiment, the term "siRNA" refers to RNA interference, which in another embodiment refers to the process of sequence-specific post-transcriptional gene silencing in animals, mediated by short interfering RNAs (siRNAs). In another embodiment, the process of post-transcriptional gene silencing is an evolutionarily-conserved cellular defense mechanism used to prevent the expression of foreign genes. Such protection from foreign gene expression evolved in one embodiment, in response to the production of double-stranded RNAs (dsRNAs) derived from viral infection or in another embodiment, from the random integration of transposon elements into a host genome via a cellular response that specifically destroys homologous single-stranded RNA of viral genomic RNA. In one embodiment, the presence of dsRNA in cells triggers the RNAi response.

In one embodiment, the term "conserved", refers to amino acid sequences comprising the peptides or nucleotides described herein, which remain in one embodiment, essentially unchanged throughout evolution, and exhibit homology among various species producing the protein.

The presence of long dsRNAs in cells stimulates, in another embodiment, the activity of a ribonuclease III enzyme referred to as dicer. Dicer is involved in one embodiment, in the processing of the dsRNA into short pieces of dsRNA known as short interfering RNAs (siRNAs). Short interfering RNAs derived from dicer activity are in another embodiment about 21 to about 23 nucleotides in length and comprise about 19 base pair duplexes. Small RNAs function in one embodiment, by base-pairing to complementary RNA or DNA target sequences. When bound to RNA, small RNAs trigger RNA cleavage in another embodiment, or translational inhibition of the target sequence in another embodiment. When bound to DNA target sequences, small interfering RNAs mediate in one embodiment, DNA methylation of the target sequence. The consequence of these events, in one embodiment, is the inhibition of gene expression, which, in another embodiment is the Stat5a, Stat3 or MeCP2 and their combination gene encoding the Stat5a, Stat3 or MeCP2 and their combination protein described herein. In one embodiment, the agent used for reducing the level or function of Stat5a, Stat3 or MeCP2 and their combination, is a siRNA specific for the nucleic acid encoding Stat5a, Stat3 or MeCP2 and their combination.

In one embodiment, the siRNA of the Stat3 or MeCP2 gene and their combination encoding the Stat3 or MeCP2 proteins and their combination described herein exhibits substantial complementarity to its target sequence. In another embodiment, "complementarity" indicates that the oligonucleotide has a base sequence containing an at least 15 contiguous base region that is at least 70% complementary, or in another embodiment at least 75% complementary, or in another embodiment at least 80% complementary, or in another embodiment at least 85% complementary, or in another embodiment at least 90% complementary, or in another embodiment at least 95% complementary, or in another embodiment 100% complementary to an-at least 15 contiguous base region present of a target gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment, the siRNA of the Stat3 or MeCP2 gene described herein is sufficiently complimentary to its target sequence. "Sufficiently complementary" refers in one embodiment to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are at least about 80% in one embodiment, or at least about 90% in another embodiment, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, 2nd ed. (Cold Spring Harbor Laboratory Press, Cold Spring Harbor, N.Y., 1989).

The term "nucleic acid" as used in connection with siRNA, refers in one embodiment to a polymer or oligomer composed of nucleotide units (ribonucleotides, deoxyribonucleotides or related structural variants or synthetic analogs thereof) linked via phosphodiester bonds (or related structural variants or synthetic analogs thereof). Thus, the term refers to a nucleotide polymer in which the nucleotides and the linkages between them are naturally occurring (DNA or RNA), as well as various analogs, for example and without limitation, peptide-nucleic acids (PNAs), phosphoramidates, phosphorothioates, methyl phosphonates, 2-O-methyl ribonucleic acids, and the like. In one embodiment, the siRNAs used in the compositions and methods of the invention, are nucleic acid sequences.

In one embodiment, the agent capable of inhibiting the function of MeCP2 or Stat3 protein in the methods described herein, is an antibody or a fragment thereof, specific against MeCP2 or Stat3. In one embodiment, the term "antibody" includes complete antibodies (e.g., bivalent IgG, pentavalent IgM) or fragments of antibodies which contain an antigen binding site in other embodiments. Such fragments include in one embodiment Fab, F(ab')$_2$, Fv and single chain Fv (scFv) fragments. In one embodiment, such fragments may or may not include antibody constant domains. In another embodiment, Fab's lack constant domains which are required for Complement fixation. ScFvs are composed of an antibody variable light chain ($V_L$) linked to a variable heavy chain ($V_H$) by a flexible hinge. ScFvs are able to bind antigen and can be rapidly produced in bacteria or other systems. The invention includes antibodies and antibody fragments which are produced in bacteria and in mammalian cell culture. An antibody obtained from a bacteriophage library can be a complete antibody or an antibody fragment. In one embodiment, the domains present in such a library are heavy chain variable domains ($V_H$) and light chain variable domains ($V_L$) which together comprise Fv or scFv, with the addition, in another embodiment, of a heavy chain constant domain ($C_{H1}$) and a light chain constant domain ($C_L$). The four domains (i.e., $V_H$-$C_{H1}$ and $V_L$-$C_L$) comprise an Fab. Complete antibodies are obtained in one embodiment, from such a library by replacing missing constant domains once a desired $V_H$-$V_L$ combination has been identified.

The Antibodies described herein can be monoclonal antibodies (mAb) in one embodiment, or polyclonal antibodies in another embodiment. Antibodies of the invention which are useful in the compositions and methods of the invention can be from any source, and in addition may be chimeric. In one embodiment, sources of antibodies can be from a mouse, or a rat, a plant, or a human in other embodiments. Antibodies of the invention which are useful for the compositions, and methods of the invention have reduced antigenicity in humans (to reduce or eliminate the risk of formation of anti-human antibodies), and in another embodiment, are not antigenic in humans Chimeric antibodies for use the invention contain in one embodiment, human amino acid sequences and include humanized antibodies which are non-human antibodies substituted with sequences of human origin to reduce or eliminate immunogenicity, but which retain the antigen binding characteristics of the non-human antibody.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXPERIMENTAL DETAILS SECTION

Materials and Methods

Cells

SUDHL1, JB6, and SUP-M2 cell lines were derived from anaplastic large T-cell lymphomas and carry the t(2;5) chromosomal translocation involving ALK and NPM genes. PB-1, 2A, 2B, Sez-4, MyLa 2059 and MyLa 3467 T-cell lines were established from patients with CTCL. HUT102B cell line represents HTLV-I-related adult type T-cell lymphoma/leukemia and Jurkat acute T-cell leukemia/lymphoblastic lymphoma. The B-cell lines: EBV-transformed (HH and MM) and derived from mantle cell (Mino, Sp49, and Sp53), diffuse large B-cell (Val, Lypn, Ly18), and Burkitt (BJAB) lymphoma. PBMC were obtained from healthy adults by centrifugation on Ficoll/Paque gradient. To obtain PHA blasts, PBMC were stimulated with the mitogen for 3 days. NPM/ALK$^+$ T-cell lymphoma tissues were obtained from the diagnostic nodal and soft tissue tumor biopsies, snap frozen and prepared as glassslide tissue sections. In all cases the diagnosis was based on cell morphology and immunophenotyping including expression of CD30 and ALK proteins. The tissue regions rich in the malignant, anaplastic large cells were utilized in the study. Native CTCL cells were obtained from patients with advanced leukemic phase of the disease and were >95% pure as determined by flow cytometry. The study was performed under IRB-approved protocols.

Treatment of the NPM/ALK$^+$ T-Cell Lines with DNMT Inhibitor

The cells were treated with 0.5 µM of 5'-aza (Sigma), with fresh medium containing 5-aza replenished every two days. The cells were harvested daily on days 1 to 7 for DNA, RNA, and protein extraction.

RT-PCR

Total cellular RNA extracted with RNeasy kit (Qiagen) was converted to cDNA with SuperScript ™ II reverse transcriptase (GIBCO/BRL) and purified on Centri-Sep columns (Princeton Separations) as described. PCR was performed in duplicate for 30 cycles in the standard reaction with primers specific for Stat5a (forward: 5'-aaatggcgggctg-gatccagg-3' (SEQ ID NO: 2); and reverse: 5'-agcgtgggat-tcaaacattc-3' (SEQ ID NO: 3)), pcDNA3 or pcDNA3-Stat5a cDNA (forward: 5'-ccactgcttactggcttatcg-3 (SEQ ID NO: 4); and reverse: 5'-ccgccagtgtgatggata-3' (SEQ ID NO: 5) and 5'-gtacagcacctgcatctgg-3' (SEQ ID NO: 6), respectively). The identity of the RT-PCR products was confirmed by DNA sequencing.

Western Blot Analysis

These experiments were performed using ECL chemiluminescence and antibodies against Stat5a, Stat5b, Stat3, ALK, SHP-1, NPM, and Actin (Santa Cruz) and p-Stat3 (Cell Signaling Technology).

DNA Methylation Analysis

After isolation with the DNeasy Tissue Kit (Qiagen), the genomic DNA was modified by bisulfite treatment using the CpGenome DNA Modification Kit (Intergen) and amplified by PCR using Stat5a specific primers (forward: 5'-taatt-taggggtttaaaagatgata-3' (SEQ ID NO: 7); and reverse: 5'-ac-ctaataaaaccgcaccgt-3' (SEQ ID NO: 8) or 5'-acctaataaaacct-cacctt-3' (SEQ ID NO: 9)) that amplify CpG island with promoter region of the Stat5a gene. PCR products were separated on agarose gel, purified using the QIAEX II gel purification kit (Qiagen), cloned into pCR2.1 vector using TA Cloning Kit (Invitrogen), amplified by PCR using the M13 primers and sequenced.

EMSA

The assays were performed as described before. In brief, nuclear proteins were extracted and incubated with biotin-labeled DNA probes 5'-GAGTATTCTAAGAAATGGATTT-GCA-3' (SEQ ID NO: 10) corresponding to the NPM gene enhancer region that contains either wild-type STAT5 GAS binding site or its two different mutants described in FIG. 4b. The protein-DNA probe complexes were separated in the acrylamide gels and transferred to nylon membranes. Blots were developed using HPR system (Pierce).

ChIP Assays

Soluble chromatin-containing lysates obtained from formaldehyde-fixed and sonicated cells were incubated with the antibodies against Sp-1, MeCP-2 or Stat5a. DNA-protein immunocomplexes were precipitated with protein A-agarose beads, treated with RNase A and proteinase K; the DNA samples were extracted with phenol/chloroform, precipitated with ethanol and PCR amplified using primers specific for Stat5a gene promoter (5'-cacattccccggctatt-3' (SEQ ID NO: 11) and 5'-acattccccggctattct-3', SEQ ID No: 21) and 3' end of the gene (5'-aaaagagtccttcctgtctcgac-3', (SEQ ID NO: 12) and 5'-ctggctccttacccttctgaCTGGCTCCTTAC-CCTTCTGA-3', (SEQ ID NO: 13)) as well as the NPM gene enhancer (5'-gcctcagctttccaagtagc-3', (SEQ ID NO: 14) and 5'-tgcctgctacttactgtgc-3', (SEQ ID NO: 15)) and 3' end (5'-ggctccttcacaaaccagag-3', (SEQ ID NO: 16) and 5'-at-gaacccatgctcaaaacc-3', (SEQ ID NO: 17)).

Plasmid Construction and Transient Transfections

A standard RT-PCR was used to clone the complete coding regions of the human Stat5a cDNA and NPM/ALK into pcDNA3 expression vector (Invitrogen). Briefly, total RNA from a healthy donor for Stat5a and NPM/ALK⁺ line (SUDHL-1) for NPM/ALK was reverse transcribed into cDNA in the presence of an oligo-d(T) primer. The cDNA was amplified by PCR with primers for Stat5a (forward: 5'-aaggtaccaaatggcgggctggatccagg-3', (SEQ ID NO: 18); and reverse: 5'-actctagaagcgtgggattcaaacattc-3', SEQ ID NO: 22) and for NPM/ALK (forward: 5'-ttaagcttcgatg-gaagattcgatggaca-3', (SEQ ID NO: 19); and reverse: 5'-aagcggccgcgctcagggcccaggctggttca-3', (SEQ ID NO: 20)), which were designed based on the sequences of human Stat5a and NPM/ALK from the GenBank (AC099811 and U04946, respectively). Each primer was designed to contain a tail that includes a specific restriction enzyme sequence (Kpn I in the 5' primer and Xba I in the 3' primer of Stat5a; Hind III in the 5' primer and Not I in the 3' primer of NPM/ALK). A 2400 bp PCR product of Stat5a was cloned at Kpn I (upstream) and Xba I (downstream) sites and 2200 bp NPM/ALK PCR fragment was cloned at Hind III (upstream) and Not I (downstream); their structural integrity was confirmed by sequence analysis. The ability of the pcDNA3-hStat5a and pcDNA-NPM/ALK plasmids to express Stat5a and NPM/ALK mRNA and proteins was verified by in vitro transcription and translation in cell lines.

In addition, GFP cDNA was cloned into pIRESpuro vector (Clontech) to serve as a transfection efficiency control. The vectors were transfected into cells using Lipofectamine-2000 Transfection kit (Invitrogen) according to the manufacturer's instructions.

siRNA Assay

Mixture of four STAT5a-, ALK-, or STAT3-specific or non-targeting siRNAs (Dharmacon) was introduced into cells at 100 nM by lipofection with Lipofectamine 2000. The procedure was repeated after 24 hrs and the cells were evaluated after additional 24 hrs and, for STAT5a, 48 hrs.

MTT Enzymatic Conversion Assay

The transfected cells were cultured at 37° C. in microtiter plates at $2 \times 10_4$/well for up to 7 days, labeled with 10 µl of MTT (Promega) at 5 mg/ml for 4 h, and solubilized overnight with 10% SDS in 0.01 M HCl. The absorbance (O.D.) was determined at 570 nm in Titertek Multiskan microtiter plate reader.

Colony Formation Assay

SUDHL-1 cells were cultured for up to 3 days in the medium alone or medium containing 5'-aza, washed and plated in the semi-solid agar for the total culture time of 21 days when the number of growing colonies was counted.

Statistical Data Analysis

The square root of the number of CpG methylation sites was analyzed using a one-way analysis of variance (ANOVA); Tukey's procedure was used to adjust for multiple comparisons.

EXAMPLE 1

Selective Loss of Stat5A Protein Expression in Malignant T Lymphocytes that Express NPM/ALK To assess the contributions of Stat5a and Stat5b to NPM/ALK-mediated cell transformation, the expression of these two proteins in the NPM/ALK⁺ T-cells and control cell populations (FIG. 1a) were examined. Whereas all normal and malignant T-cell populations including three NPM/ALK⁺ T-cell lines (JB6, SUDHL-1, and SUP-M2) expressed Stat5b, none of the NPM/ALK⁺T-cell lines expressed the Stat5a protein. In contrast, the normal resting, T-cell rich peripheral blood mononuclear cells (PBMC), PBMC activated with mitogen (PHA), either alone or in combination with IL-2, and malignant, NPM/ALK⁻ T-cell line 2A all expressed Stat5a. Interestingly, resting PBMC displayed both, truncated and full-length forms$_{26}$ of Stat5a, while the activated PBMC and 2A cells expressed only the full-length form. To explore further if the Stat5a loss is specific among malignant lymphocytes to those that express NPM/ALK. Additional seven T-cell and nine B-cell lines derived from different types of lymphomas that are NPM/ALK were examined. As shown in FIG. 1b, all expressed full-length Stat5a. The lack of Stat5a expression was identified also in the native ALK₊ TCL tissues in which variable but in general small amount of Stat5a protein (presumably derived from non-neoplastic cells admixed with the malignant cells) were detected (FIG. 1c, left panel). In contrast, biologically related but NPM/ALK−, native cutaneous T-cell lymphoma (CTCL) cells strongly expressed the protein (FIG. 1c, right panel). To determine if expression of Stat5a protein can be induced in the NPM/ALK⁺ T lymphocytes, such cells were stimulated with PHA or PHA and IL-2. However, the stimulation did not lead to Stat5a expression (FIG. 1d).

EXAMPLE 2

NPM/ALK+ T Cells Fail to Express Stat5A Transcript

To determine whether the lack of the Stat5a protein expression represents a pre- or posttranscriptional event, the NPM/ALK+ T-cell lines for expression of Stat5a mRNA were examined. RT-PCR demonstrated that all three cell lines did not express Stat5a mRNA and that its expression could not be induced by PHA or PHA/IL-2 stimulation (FIG. 1e).

EXAMPLE 3

Stat5A Gene DNA is Structurally Intact in the NPM/ALK+ T Cells

To determine whether the lack of Stat5a expression stems from the structural abnormalities of its genomic DNA, the Stat5a gene sequence using the GenBank-deposited sequence (AC099811) as the reference was analyzed. No deletions or point mutations were identified in either exons or splice junctions of the gene in two NPM/ALK+ T-cell lines SUDHL-1 and JB6.

EXAMPLE 4

Figure 2:
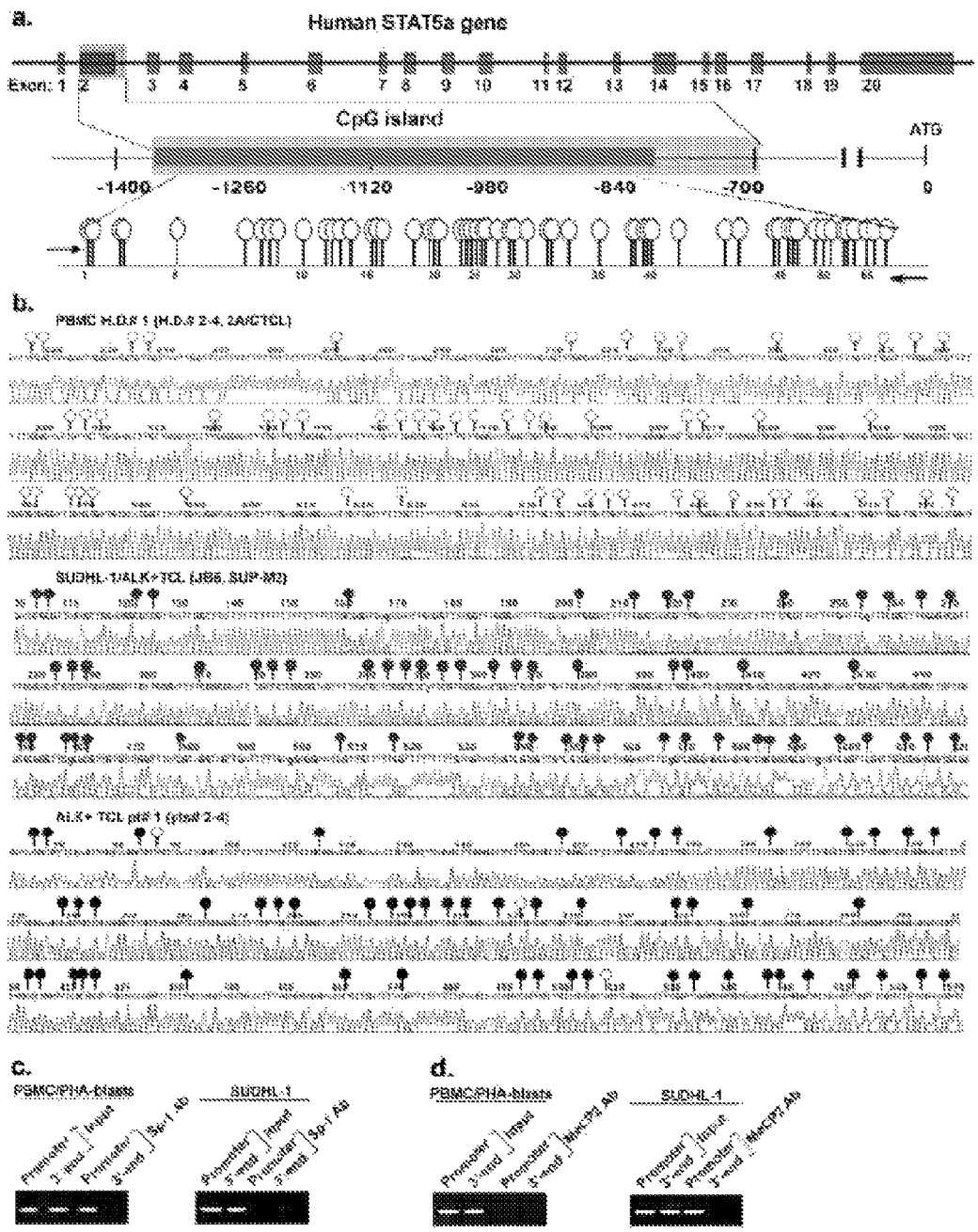
FIG. 2. shows methylation of CpG island within Stat5a gene promoter region in NPM/ALK$^+$ T cells.

Methylation of the CpG Island within the Stat5a Gene Promoter in NPM/ALK+ T-Cells To determine if methylation of the CpG island within the Stat5a gene promoter region (FIG. 2a) may be responsible for the lack of Stat5a expression in the NPM/ALK+ T cells, CpG methylation status of the island was examined, focusing on its main part that contains 57 CpG sites. None of the CpG sites was methylated in the PBMC from four healthy donors (4-6 DNA cloned fragments per donor) as well as malignant NPM/ALK- T-cell line 2A (FIG. 2b depicts representative results). In contrast, methylation of all 57 CpG sites was identified in all clones from three NPM/ALK+ T-cell lines (4-6 clones per cell line). In NPM/ALK+ T-cell lymphoma tissues derived from four patients, 21 of the total of 24 clones displayed methylation of 51-55 of the 57 sites. The remaining 3 clones displayed no methylation of the CpG sites and in all likelihood were derived from the non-neoplastic cells.

EXAMPLE 5

Lack of SP-1 and the Presence of MeCP2 Binding to the Stat5A Promoter in NPM/ALK+ T Cells Using the chromatin immunoprecipitation (ChIP) assay, methylation of the Stat5a gene promoter prevents binding of the known Stat5a gene transcription activator Sp-1 and is associated with binding of the MeCP2 protein involved in stabilizing the epigenetic gene silencing was examined. Whereas Sp-1 binding to the promoter could be easily detected in PHA-activated PBMC, no such binding was present in the NPM/ALK+ T-cell line SUDHL-1 (FIG. 2c). In contrast, there was no binding to the promoter of MeCP2 in the PHA/PBMC cells but strong binding of the protein in the SUDHL-1 cells (FIG. 2d). These findings suggest that CpG island methylation of the Stat5a promoter is responsible for transcriptional silencing of the Stat5a gene.

EXAMPLE 6

Figure 3:
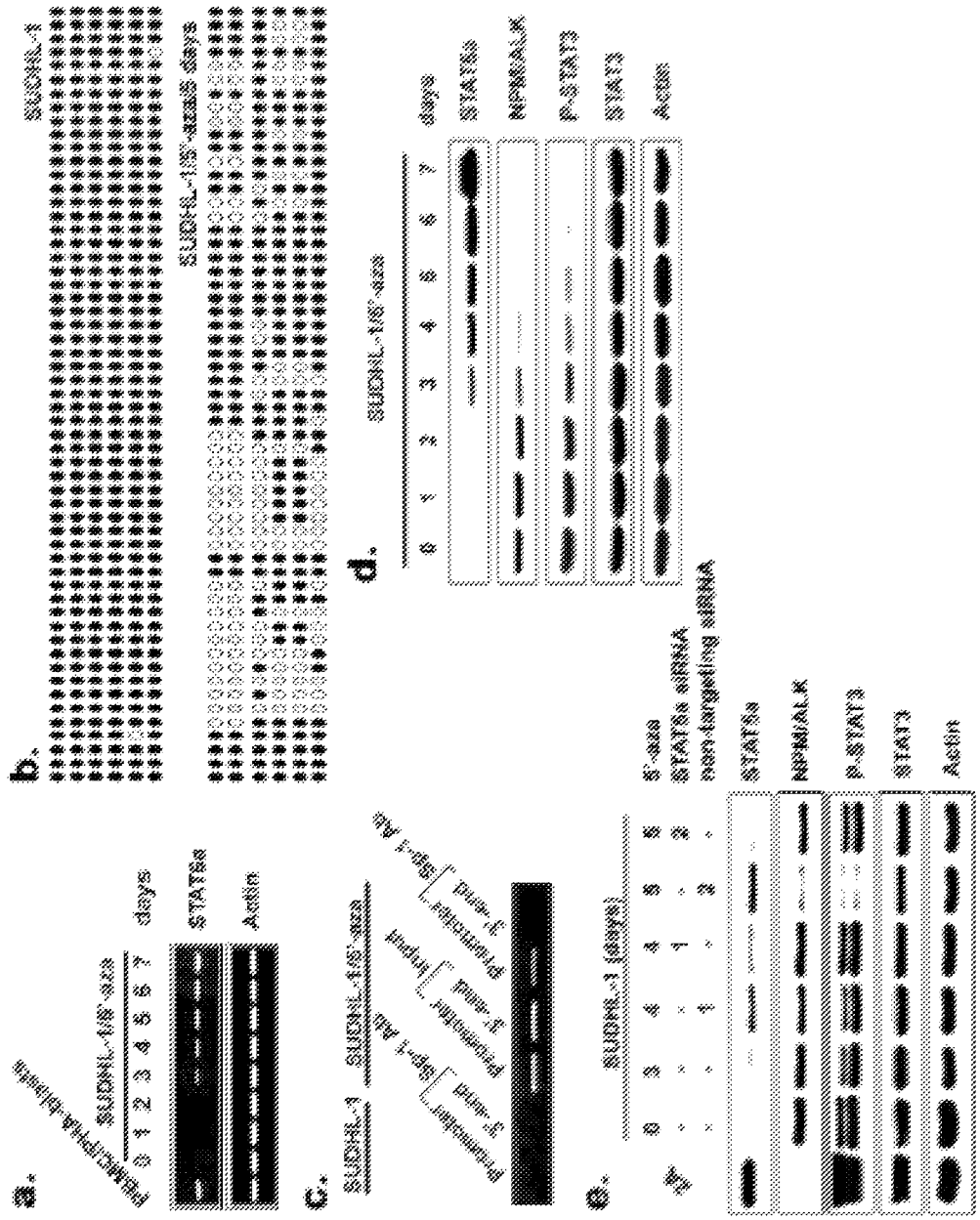
FIG. 3. shows demethylation of Stat5a promoter region results in expression of Stat5a and suppression of NPM/ALK expression. NPM/ALK$^+$ SUDHL-1 cells were treated with DNMT inhibitor 5'-aza-2'-deoxy-cytidine (5'-aza) for up to seven days.
Figure 5:
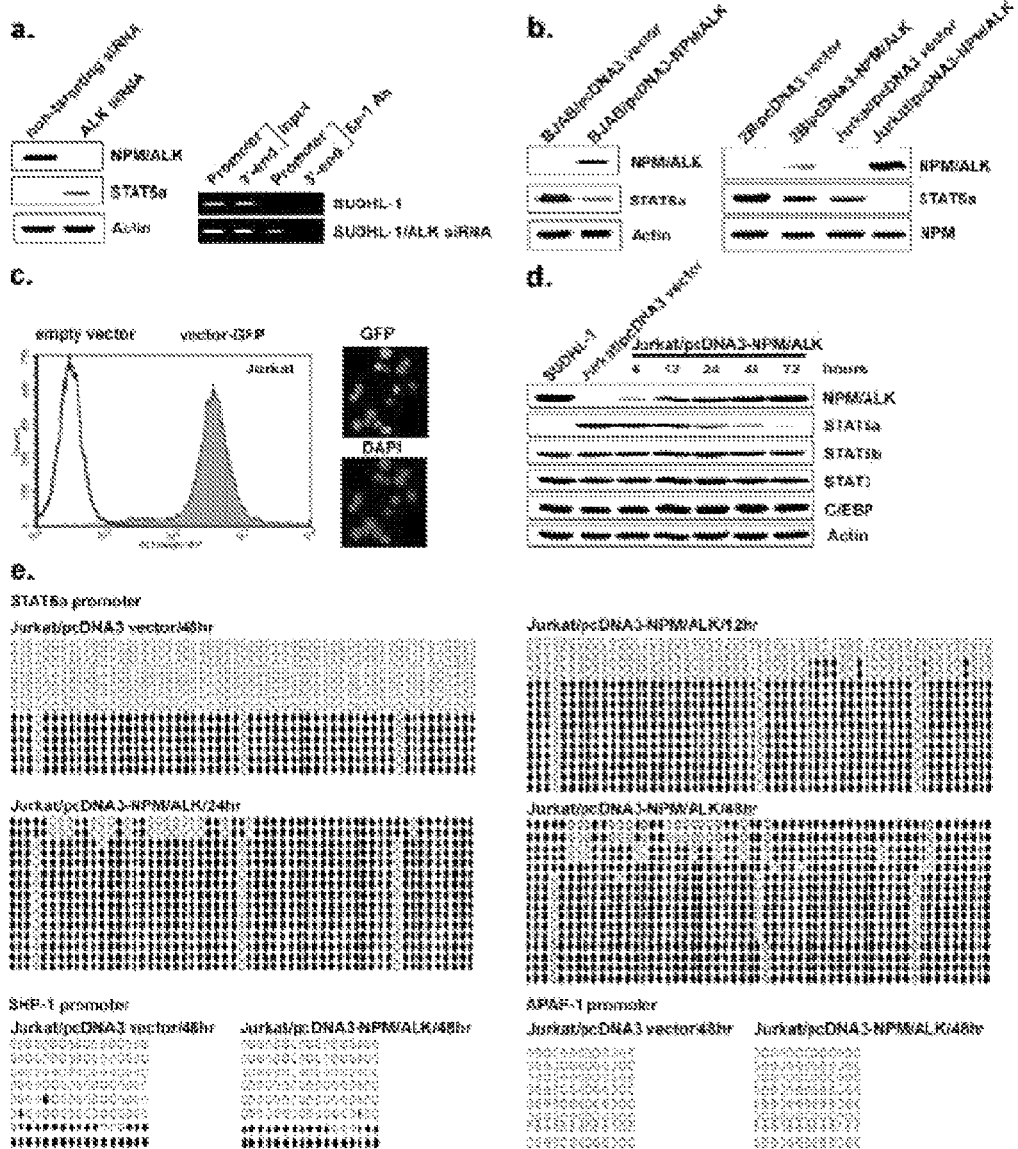
FIG. 5. shows that NPM/ALK promotes epigenetic silencing of Stat5a gene.

Demethylation of the Stat5A Gene Promoter's CpG Island Results in Activation of the Stat5A Gene To determine whether removal of the promoter's CpG methylation leads to Stat5a expression, the NPM/ALK+ T-cells were treated with a DNMT inhibitor, 5'-aza-2'-deoxy-cytidine (5'-aza). The treatment led in the SUDHL-1 (FIG. 3a) and JB6 cells to gradual, time-dependent expression of Stat5a mRNA. To examine the 5'-aza-induced changes in methylation of the Stat5a gene promoter, bisulfate-aided analysis of its DNA sequence was performed. As shown in FIG. 3b, 5-day treatment of the SUDHL-1 cells resulted in partial promoter demethylation that affected from 28% to 47% of the CpG sites. Noteworthy, there were areas of preferential demethylation, with a minority (13%) of the CpG sites becoming unmethylated in at least 5 of the 6 clones studied; the majority undergoing demethylation in various proportions of the clones, and one third of the sites remaining fully methylated. As shown in FIG. 3c, the 5'-aza-induced CpG demethylation permitted binding of Sp-1 to the Stat5a promoter.

EXAMPLE 7

Expression of Stat5A is Associated with Inhibition of NPM/ALK Expression

As expected from the above data, 5'-aza treatment led also in the ALK+ TCL cells to expression of the Stat5a protein (FIG. 3d and S2). However, the increasing expression of Stat5a was associated with in the cells with a steady decrease in expression of NPM/ALK (FIG. 3d). The steady decrease in NPM/ALK expression resulted in gradual dephosphorylation of its crucial target $STAT3_{25}$. Expression of total STAT3 and actin was not affected indicating selective nature of inhibition of the NPM/ALK expression. To demonstrate directly the causative relationship between the STAT5a expression and NPM/ALK loss, the 5'-aza-treated cells were transfected with the STAT5a-specific and control, non-targeting siRNA. Whereas the STAT5a depletion protected NPM/ALK expression, the non-targeting siRNA did not (FIG. 3e).

EXAMPLE 8

Stat5A Directly Down-Regulates Expression of the NPM/ALK Gene by Binding to the Hybrid Gene's Enhancer and Intron 14

Figure 4:
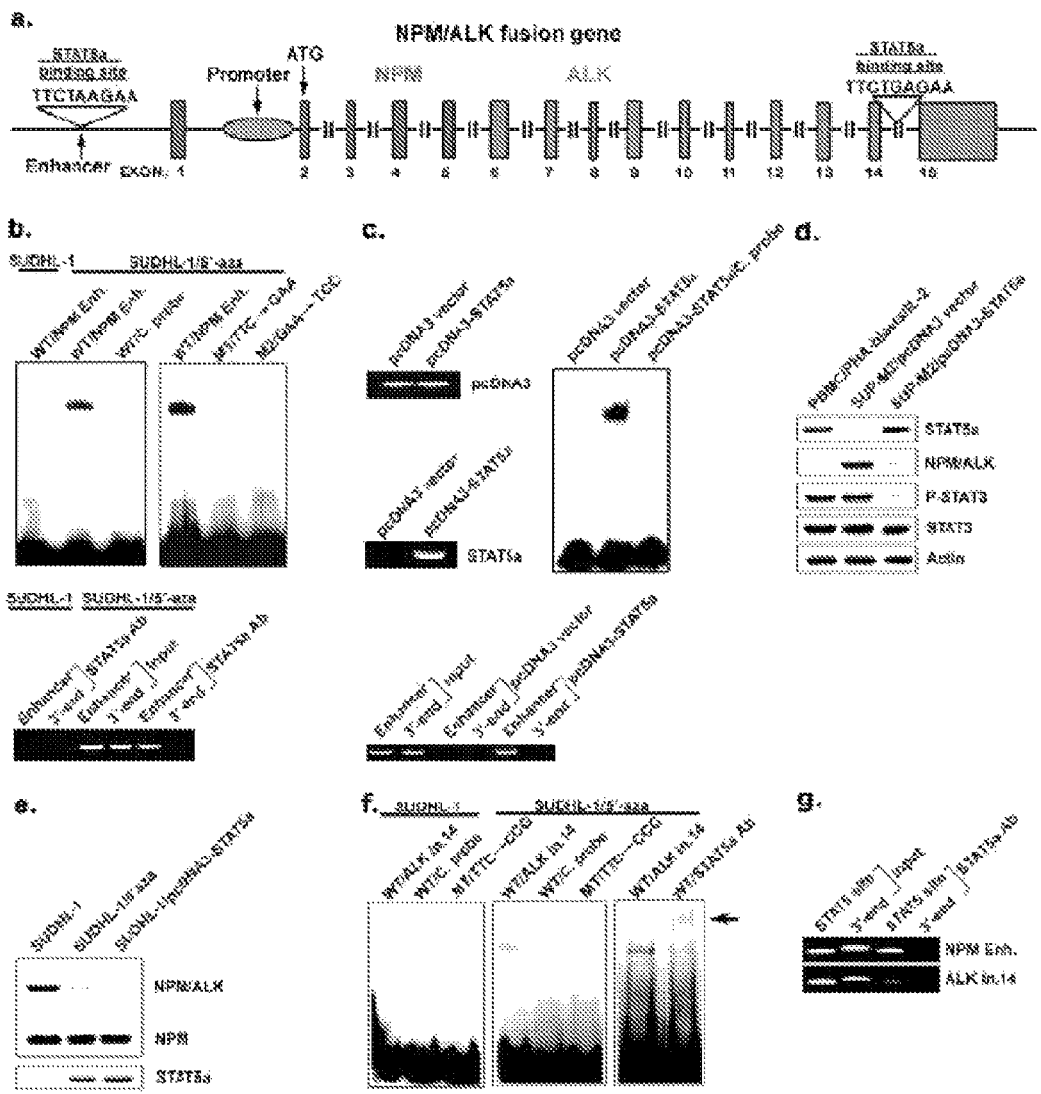
FIG. 4. shows that Stat5a binds to enhancer of the NPM/ALK gene and down-regulates expression of the gene.

The inhibition of NPM/ALK expression strongly suggested that Stat5a might act as a direct transcription inhibitor of the NPM/ALK gene. DNA sequence analysis of the gene regulatory domains identified within the enhancer region (FIG. 4a) GAS sequence (TTCTAAGAA, SEQ ID NO: 23) consistent with the STAT5 binding site (TTCC/tT/cagG/aGAA). No GAS sites were seen in the promoter region. To determine if Stat5a binds to the enhancer's site, an electrophoretic mobility shift assay (EMSA) was performed with the corresponding 25-mer DNA probe. As shown in FIG. 4b (upper panel), nuclear protein extracts from the SUDHL-1 cells treated with 5'-aza, but not from the control, untreated cells, displayed strong binding to the probe. The binding was abrogated when the protein extract was pretreated with 25-fold excess of the unlabeled "cold" probe. The binding was also abolished when the labeled probes contained small, 3-base substitutions of either of the TTC or GAA backbone sequence, providing further evidence for its specificity. ChIP assay performed to document Stat5a binding to the NPM/ALK enhancer in vivo, yielded similar result (FIG. 4b, lower panel). Accordingly, the untreated SUDHL-1 cells generated no enhancer-specific PCR product when their Stat5a-antibody immunoprecipitate was examined. In contrast, the immunoprecipitate from the SUDHL-1 cells treated with 5'-aza yielded a strong PCR band.

To demonstrate directly that down-regulation of NPM/ALK expression is mediated by Stat5a, two NPM/ALK$^+$ T-cell lines SUDHL-1 and SUP-M2 were transfected with the Stat5a-containing pcDNA3 vector or control, empty vector. Effectiveness of the transfections was demonstrated by RT-PCR using primer pairs that are specific for either the pcDNA3 vector or the pcDNA3-Stat5a construct (FIG. 4c, upper left panels). Similar to the 5'-aza-induced endogeneous Stat5a, the transfected Stat5a bound to the identified GAS site in vitro (right panel) and to the enhancer in vivo (lower panel). Furthermore, the transfected Stat5a, but not the pcDNA3 vector, inhibited expression of NPM/ALK protein and phosphorylation of its key target STAT3 (FIG. 4d). As shown in supplementary figure S3a, there was a complete inverse correlation between the concentration of the transfected STAT5a and the endogeneous NPM/ALK. There was also a very similar inverse correlation between the STAT5a expression and the resulting NPM/ALK loss and cell growth as determined in the MTT conversion assay (S3b). Of note, transfection of STAT5a into ALK– Jurkat T-cells had no negative effect on their growth. Because the native NPM gene and NPM/ALK hybrid gene share the same enhancer/promoter region, next it was asked whether STAT5a affects also expression of the intact NPM. As shown in FIG. 4e and S3a, the effect of STAT5a was strictly selective for NPM/ALK because treatment of the NPM/ALK$^+$ T cells with 5'-aza or transfection with Stat5a inhibited expression of NPM/ALK but had no effect on expression of the native NPM. This result suggested that the ALK portion of the NPM/ALK gene contributes to the suppressive activity of Stat5a, possibly by providing via DNA looping additional Stat5a binding site to permit formation of Stat5a tetramers. Screening of the ALK component of the NPM/ALK gene identified a potential Stat5a binding site in the intron 14 (depicted in FIG. 4a). The site was indeed able to bind specifically Stat5a as demonstrated in the EMSA and EMSA/supershift (FIG. 4f) as well as ChIP (FIG. 4g) assays.

EXAMPLE 9

NPM/ALK Induces Epigenetic Silencing of the Stat5A Gene

Because Stat5a silencing was restricted amongst various transformed T- and B-cell populations to the NPM/ALK$^+$ T-cells, the ability of NPM/ALK itself to play a role in induction of the silencing was examined. As shown in FIG. 5a, siRNA-mediated inhibition of NPM/ALK expression indeed resulted in expression of the Stat5a protein (left panel) that was associated with binding of the transcription activator Sp-1 to the Stat5a gene promoter (right panel). To provide additional evidence that NPM/ALK induces the Stat5a gene silencing, NPM/ALK gene was transfected into three different B- and T-cell lymphoma cell lines (BJAB and 2B and Jurkat, respectively). As shown in FIG. 5b, NPM/ALK inhibited expression of Stat5a protein proportionately to the efficiency of transfection with Jurkat cells yielding the most clear-cut result. The high transfection efficiency of Jurkat cells was confirmed by introducing into the cells a GFP-containing vector that became strongly expressed in essentially all cells (FIG. 5c). To examine kinetics of the Stat5a protein loss induced by NPM/ALK, Stat5a expression was determined in the NPM/ALK-transfected Jurkat cells at five different time points (FIG. 5d). The decrease in Stat5a protein concentration was unequivocal by 48 hr and seemed almost total by 72 hr. Noteworthy, none of the several control proteins including Stat5b, displayed any changes in their expression confirming that NPM/ALK specifically targets Stat5a. As shown in FIG. 5e, Stat5a protein loss in the NPM/ALK-transfected Jurkat cells was preceded by CpG methylation of the Stat5a gene promoter. Interestingly, roughly half of the DNA clones from the control Jurkat cells, either parental (not shown) or transfected with the empty vector, displayed almost complete CpG methylation of the Stat5a promoter suggesting constitutive epigenetic silencing of one of the alleles. The promoter methylation seemed increased at 12 hr post transfection with NPM/ALK and was almost complete at 24 hr and 48 hr (FIG. 5e) and statistically different from the empty vector transfected cells (p=0.04 and p=0.08, respectively). In contrast, analysis of promoters of the two other randomly chosen genes, SHP-1 and APAF-1 showed no increase in the CpG methylation providing further evidence that the NPM/ALK-induced promoter methylation is specific for the Stat5a gene.

EXAMPLE 10

Involvement of Stat3 in the Silencing of the Stat5A Gene

Because Stat3 is the main effector of the NPM/ALK-mediated oncogenesis and does promote epigenetic gene silencing in malignant T cells by inducting expression of DNMT1 and by interacting with this DNA methyltransferase, next it was examined whether Stat3 is involved in silencing of the Stat5a gene. SiRNA-mediated inhibition of Stat3 expression indeed resulted in the time-dependent Stat5a expression (FIG. 6a). It also led to demethylation of the Stat5a promoter (p<0.0001 for both 48 h and 72 h as compared to untreated cells) in the highly distinct pattern (FIG. 6b). Finally, it restored binding of Sp-1 and induced loss of binding of MeCP2 to the Stat5a promoter (FIG. 6c) supporting the key role of Stat3 in silencing of the Stat5a gene.

EXAMPLE 11

Inhibition of DNMT Suppresses Growth of the NPM/ALK$^+$ T Cells

The effects of 5'-aza on growth of NPM/ALK$^+$ T cells using an MTT enzymatic conversion and colony formation assays were examined. As shown in FIG. 6d, the 5'-aza treatment-resulted in a potent, time-dependent inhibition of cell growth that was relatively most pronounced by day 5. Similarly, 5'-aza profoundly inhibited clonogenic capacity of the NPM/ALK$^+$ cells (FIG. 6e). Of note, the inhibitor exerted a long-lasting effect on the cells, since their exposure to 5'-aza for only 1 day reduced the number of colonies counted on day 21 by >85% and exposure for 3 days totally abrogated the colony formation.

Stat3 and, to the lesser degree, Stat5 are well recognized as oncoproteins and their persistent activation has been identified in a large spectrum of lymphoid and nonlymphoid malignancies[36]. They promote oncogenesis by modulating several key functions of the malignant cells such as survival, proliferation, migration, invasion, induction of angiogenesis, and evasion of the immune response. However, it has been observed that in breast carcinoma Stat5 phosphorylation confers good prognosis seemingly by the Stat5-mediated inhibition of metastatic capacity of the malignant cells via promoting their expression of E-cadherin. These results indicated that on occasion Stat5 may inhibit rather than promote oncogenesis.

The present novel mechanism of regulation of expression of Stats, specifically of Stat5a, and provides evidence that Stat5a can act as a direct tumor suppressor. Furthermore, it demonstrates that this novel tumor suppressor activity is accomplished by targeting expression of the key oncogene. Whereas previous studies from numerous laboratories$_{36}$ including ours$_{5,25,34,35}$ focused on the role and mechanisms of Stat activation in the malignant cell transformation, regulation of Stat genes did not receive much attention due to the ubiquitous expression of Stats in normal and, seemingly, malignant cells. Furthermore, most anti-Stat5 antibodies, in particular the ones against the phospho-forms, react with both Stat5a and Stat5b, precluding identification of changes in expression and activation of only one of them.

Here it is shown that expression of Stat5a is lost in malignant cells, in this case in T lymphocytes transformed by NPM/ALK tyrosine kinase, and that the Sta5a expression loss results from epigenetic gene silencing. Furthermore, it was demonstrate that the epigenetic silencing is promoted by NPM/ALK documenting that this oncogenic tyrosine kinase is capable of inducing epigenetic silencing of tumor suppressor genes. NPM/ALK induces the Stat5a gene silencing by activating Stat3 shown by us recently to epigenetically silence another tumor suppressor, SHP-1 phosphatases. The distinct pattern and relatively limited nature of the Stat5a promoter demethylation following depletion of NPM/ALK and, in particular, Stat3 suggest that demethylation of the specific CpG "hot spots" within the promoter is sufficient to foster its transcriptional activation. They also suggest that, in addition to Stat3, NPM/ALK utilizes other factors, or mechanisms, to methylate certain areas of the Stat5a promoter. It is striking that Stat5a exerts its tumor suppressor function by reciprocally impairing expression of NPM/ALK. The present findings indicate that the loss of Stat5a expression is critical for the NPM/ALK-mediated oncogenesis by permitting uninterrupted transcription of the NPM/ALK gene. Taken together, the above observations indicate existence of a "double-negative" feedback loop in which an oncogenic tyrosine kinase, NPM/ALK, succeeds in being persistently expressed by inhibiting expression of the transcriptional inhibitor of its own gene, Stat5a. The current data also demonstrate that Stat5a and Stat5b can play opposite roles in malignant transformation of the same target cells. In contrast to the Stat5a gene silencing, Stat5b is expressed in the NPM/ALK-transformed cells and, more importantly, persistently activated by the chimeric kinase. It contributes to the NPM/ALK-mediated oncogenesis by promoting cell growth and survival.

Present findings have also potential therapeutic implications for NPM/ALK[+] T-cell lymphomas and, possibly, other malignancies that express chimeric tyrosine kinases. Whereas translational research efforts concentrate currently on inhibition of the kinase activity, with targeting of BCR/ABL being the prime example$_{42}$, this approach by itself is not curative and over time leads to the development of drug resistance. Suppressing expression of such kinases, in addition to inhibiting their enzymatic activity, may prove therapeutically beneficial. DNMT inhibitors such as 5'-aza that have already been successfully applied clinically in hematologic malignancies, so far on an empirical basis$_{43}$, may offer complementary therapeutic approach by directly inducing expression of the epigenetically silenced transcription inhibitors that might target the oncogenic kinases. The ability of the NPM/ALK-transformed T cells to express Stat5a upon treatment with 5'-aza and suppress NPM/ALK expression and, as a consequence, profoundly inhibit cell growth strongly supports this notion.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed:

1. A method of treating a malignancy expressing a chimeric tyrosine kinase in a subject, the method comprising the step of administering to the subject a composition comprising an agent in an effective amount to increase expression of Stat5a protein in the malignancy, wherein said agent is a small molecule chemical compound, wherein the small molecule chemical compound is a DNA Methyltransferase (DNMT) inhibitor, and wherein the chimeric tyrosine kinase is an ALK$^+$ chimeric tyrosine kinase.

2. The method of claim 1, whereby the composition further comprises an agent capable of inhibiting the expression or function of a methylated DNA capping family (MBD) protein, Stat3 or their combination.

3. The method of claim 2, wherein the methylated DNA capping family (MBD) protein is Methylation binding domain protein.

4. The method of claim 2, whereby the agent capable of inhibiting the function of a methylated DNA capping family (MBD) protein is an antibody or a fragment thereof, specific against a methylated DNA capping family (MBD) protein.

5. The method of claim 4, whereby the agent capable of inhibiting the function of Methylation binding domain protein, or Stat3, is a small molecule chemical compound.

6. The method of claim 4, whereby the agent capable of inhibiting the expression of a methylated DNA capping family (MBD) protein is a siRNA, a polyamide, a triple-helix-forming agent, an antisense RNA, a synthetic peptide nucleic acids (PNAs), an agRNA, a LNA/DNA copolymer, a small molecule chemical compound, or a combination thereof, specific against a nucleotide sequence encoding a methylated DNA capping family (MBD) protein, or Stat3.

7. The method of claim 1, wherein the DNMT inhibitor is 5'-aza-2'-deoxycytidine, or 5-azacytidine.

8. The method of claim 1, wherein the malignancy is a lymphoma, leukemia, sarcoma, or carcinoma.

9. The method of claim 8, wherein the malignancy is a lymphoma.

10. The method of claim 1, wherein the chimeric tyrosine kinase is NPM/ALK.

11. The method of claim 9, wherein the lymphoma is an anaplastic large cell lymphoma.

* * * * *

UNITED STATES PATENT AND TRADEMARK OFFICE
CERTIFICATE OF CORRECTION

PATENT NO. : 9,486,469 B2  
APPLICATION NO. : 12/681327  
DATED : November 8, 2016  
INVENTOR(S) : Mariusz A. Wasik et al.

It is certified that error appears in the above-identified patent and that said Letters Patent is hereby corrected as shown below:

In the Specification

In Column 1, Line 15, the following paragraph should be inserted:
-- GOVERNMENT INTEREST STATEMENT
This invention was made with government support under grant numbers R01 CA096856 and R01 CA089194 awarded by the National Institutes of Health. The government has certain rights in the invention. --

Signed and Sealed this
Fifth Day of September, 2017

Joseph Matal
*Performing the Functions and Duties of the*
*Under Secretary of Commerce for Intellectual Property and*
*Director of the United States Patent and Trademark Office*